US011376079B2

(12) United States Patent
Pandya

(10) Patent No.: US 11,376,079 B2
(45) Date of Patent: Jul. 5, 2022

(54) SYSTEM AND TECHNIQUE FOR ACCESSING EXTRA ARTICULAR LESIONS OR ABNORMALITIES OR INTRA OSSEOUS LESIONS OR BONE MARROW LESIONS

(71) Applicant: Rajiv D. Pandya, Atlanta, GA (US)

(72) Inventor: Rajiv D. Pandya, Atlanta, GA (US)

( * ) Notice: Subject to any disclaimer, the term of this patent is extended or adjusted under 35 U.S.C. 154(b) by 58 days.

(21) Appl. No.: 16/713,857

(22) Filed: Dec. 13, 2019

(65) Prior Publication Data

US 2020/0113633 A1    Apr. 16, 2020

Related U.S. Application Data

(60) Continuation-in-part of application No. 16/118,750, filed on Aug. 31, 2018, now Pat. No. 10,716,632, (Continued)

(51) Int. Cl.
*A61B 17/17* (2006.01)
*A61B 34/20* (2016.01)
(Continued)

(52) U.S. Cl.
CPC .......... *A61B 34/20* (2016.02); *A61B 17/1764* (2013.01); *A61B 17/34* (2013.01);
(Continued)

(58) Field of Classification Search
CPC ............ A61B 17/1675; A61B 17/1703; A61B 17/1714; A61B 17/1717; A61B 17/1725;
(Continued)

(56) References Cited

U.S. PATENT DOCUMENTS

| 4,257,411 A | 3/1981 | Cho |
| 4,672,957 A | 6/1987 | Hourahane |

(Continued)

FOREIGN PATENT DOCUMENTS

| GB | 2230453 | 10/1990 |
| WO | 2009107121 | 9/2009 |

OTHER PUBLICATIONS

Rotator Cuff Tears and Treatment Options, Article 2007, pp. 1-9 American Academy of Orthopaedic Surgeons, Rosemont IL, Rotator Cuff Tear, 2008, pp. 1-3 ehealth MD.
(Continued)

*Primary Examiner* — Anu Ramana
(74) *Attorney, Agent, or Firm* — David L. King

(57) ABSTRACT

An improved low cost, preferably disposable instrument guide adapted to carry an access instrument used in accessing a compromised portion of a bone structure has a single piece guide body. The guide body has a first referencing arm and second referencing arm. The first referencing arm has a first end portion, wherein the first end portion of the first referencing arm has a reference structure integral therewith and wherein the reference structure defines a virtual axis. The second referencing arm is integral to the first reference arm and has at least one guide opening with a guide axis extending to intersect the virtual axis. The at least one guide opening is located at a fixed angle on the second referencing arm.

30 Claims, 36 Drawing Sheets

Related U.S. Application Data which is a continuation-in-part of application No. 15/889,883, filed on Feb. 6, 2018, now Pat. No. 10,441,368, which is a division of application No. 15/265,178, filed on Sep. 14, 2016, now Pat. No. 9,925,010, which is a continuation-in-part of application No. 15/080,980, filed on Mar. 25, 2016, now Pat. No. 10,064,633, which is a continuation of application No. 15/080,947, filed on Mar. 25, 2016, now Pat. No. 10,064,632.

(60) Provisional application No. 62/297,478, filed on Feb. 19, 2016.

(51) Int. Cl.

| | | |
|---|---|---|
| *A61B 17/34* | (2006.01) | |
| *A61B 90/11* | (2016.01) | |
| *A61B 34/10* | (2016.01) | |
| *A61B 17/88* | (2006.01) | |
| *A61B 17/56* | (2006.01) | |

(52) U.S. Cl.
CPC .......... *A61B 17/3472* (2013.01); *A61B 90/11* (2016.02); *A61B 17/8805* (2013.01); *A61B 2017/3405* (2013.01); *A61B 2017/564* (2013.01); *A61B 2034/107* (2016.02); *A61B 2034/2046* (2016.02)

(58) Field of Classification Search
CPC ............ A61B 17/1764; A61B 17/1767; A61B 17/1739
See application file for complete search history.

(56) References Cited

U.S. PATENT DOCUMENTS

| | | |
|---|---|---|
| 4,722,331 A | 2/1988 | Fox |
| 4,739,751 A | 4/1988 | Sapega et al. |
| 4,781,182 A | 11/1988 | Purnell et al. |
| 4,920,958 A | 5/1990 | Walt et al. |
| 5,112,337 A | 5/1992 | Paulos et al. |
| 5,163,940 A | 11/1992 | Bourque |
| 5,330,468 A | 7/1994 | Burkhart |
| 5,403,322 A * | 4/1995 | Herzenberg ......... A61B 17/171 606/98 |
| 5,409,493 A * | 4/1995 | Greenberg ............. A61B 17/02 606/79 |
| 5,556,428 A | 9/1996 | Shah |
| 5,562,669 A | 10/1996 | Mcguire |
| 5,669,917 A | 9/1997 | Sauer et al. |
| 5,671,695 A | 9/1997 | Schroeder |
| 5,681,333 A | 10/1997 | Burkhart et al. |
| 5,766,179 A | 9/1998 | Faccioli et al. |
| 5,895,425 A | 4/1999 | Grafton et al. |
| 6,120,511 A | 9/2000 | Chan |
| 6,132,433 A | 10/2000 | Whelan |
| 6,306,138 B1 | 10/2001 | Clark et al. |
| 6,325,804 B1 | 12/2001 | Wenstrom et al. |
| 6,517,546 B2 | 2/2003 | Whittaker et al. |
| 6,537,319 B2 | 3/2003 | Whelan |
| 6,610,064 B1 | 8/2003 | Goble et al. |
| 6,623,524 B2 | 9/2003 | Schmieding |
| 6,716,217 B2 | 4/2004 | Mckernan et al. |
| 6,926,720 B2 | 8/2005 | Castaneda |
| 7,025,786 B2 | 4/2006 | Goble et al. |
| 7,032,599 B2 | 4/2006 | May et al. |
| 7,056,340 B2 | 6/2006 | McKeman et al. |
| 7,175,632 B2 | 2/2007 | Singhatat et al. |
| 7,201,756 B2 | 4/2007 | Ross |
| 7,270,666 B2 | 9/2007 | Lombardo et al. |
| 7,338,492 B2 | 3/2008 | Singhatat et al. |
| 7,458,975 B2 | 12/2008 | May et al. |
| 7,491,206 B2 | 2/2009 | Whittaker et al. |
| 7,569,059 B2 | 8/2009 | Cerundolo |
| 7,575,578 B2 * | 8/2009 | Wetzler .................. A61B 17/17 606/96 |
| 7,594,922 B1 | 9/2009 | Goble et al. |
| 7,594,930 B2 | 9/2009 | Warlick et al. |
| 7,674,290 B2 | 3/2010 | McKernan et al. |
| 7,678,138 B2 | 3/2010 | Fitts et al. |
| 7,713,300 B2 | 5/2010 | Meridew et al. |
| 7,766,964 B2 | 8/2010 | Stone et al. |
| 7,955,341 B2 | 6/2011 | Cerundolo |
| 7,998,203 B2 | 8/2011 | Blum |
| 8,088,128 B2 | 1/2012 | May et al. |
| 8,221,454 B2 | 7/2012 | Schaffhausen |
| 8,251,998 B2 | 8/2012 | Hoeppner et al. |
| 8,292,921 B2 | 10/2012 | Stone et al. |
| 8,323,291 B2 | 12/2012 | Dienst et al. |
| 8,382,835 B2 | 2/2013 | Meridew et al. |
| 8,435,292 B2 | 5/2013 | Whittaker |
| 8,491,595 B2 * | 7/2013 | Volpi ................. A61B 17/1714 606/96 |
| 8,500,740 B2 | 8/2013 | Bojarski et al. |
| 8,512,405 B2 | 8/2013 | Baird |
| 8,551,123 B2 | 10/2013 | Pandya |
| 8,579,974 B2 | 11/2013 | Pandya |
| 8,617,166 B2 | 12/2013 | Hanson et al. |
| 8,617,176 B2 | 12/2013 | Lizardi et al. |
| 8,821,504 B2 | 9/2014 | Sharkey et al. |
| 8,864,768 B2 | 10/2014 | Hanson et al. |
| 8,906,032 B2 | 12/2014 | Hansen et al. |
| 8,951,261 B2 | 2/2015 | Sharkey et al. |
| 9,033,987 B2 | 5/2015 | Hanson et al. |
| 9,119,721 B2 | 9/2015 | Sharkey et al. |
| 9,138,187 B2 | 9/2015 | Sharkey |
| 9,259,257 B2 | 2/2016 | Bagga et al. |
| 9,271,835 B2 | 5/2016 | Bagga et al. |
| 9,351,746 B2 | 5/2016 | Hanson et al. |
| 9,351,835 B2 | 5/2016 | Sharkey et al. |
| 9,386,996 B2 | 7/2016 | Hanson et al. |
| 2001/0053934 A1 | 12/2001 | Schmieding |
| 2003/0065391 A1 | 4/2003 | Re et al. |
| 2003/0167090 A1 | 9/2003 | Chervitz et al. |
| 2003/0176919 A1 | 9/2003 | Schmieding |
| 2004/0059415 A1 | 3/2004 | Schmieding |
| 2004/0087978 A1 | 5/2004 | Velez et al. |
| 2004/0194789 A1 | 10/2004 | Whelan |
| 2004/0225358 A1 | 11/2004 | Goble et al. |
| 2005/0065533 A1 | 3/2005 | Magen et al. |
| 2005/0149187 A1 | 7/2005 | Clark et al. |
| 2006/0149259 A1 | 7/2006 | May et al. |
| 2006/0235516 A1 | 10/2006 | Cavazzoni |
| 2006/0241657 A1 | 10/2006 | Cerundolo |
| 2006/0265063 A1 | 11/2006 | Goble et al. |
| 2007/0162123 A1 | 7/2007 | Whittaker et al. |
| 2007/0208356 A1 | 9/2007 | Cerundolo |
| 2007/0233151 A1 | 10/2007 | Chudik |
| 2008/0058929 A1 | 3/2008 | Whelan |
| 2008/0154271 A1 | 6/2008 | Berberich et al. |
| 2009/0069846 A1 | 3/2009 | Bull et al. |
| 2009/0187244 A1 | 7/2009 | Dross |
| 2010/0312341 A1 | 12/2010 | Kaiser et al. |
| 2010/0324676 A1 | 12/2010 | Albertorio et al. |
| 2011/0153018 A1 | 6/2011 | Walters et al. |
| 2012/0095556 A1 | 4/2012 | Re et al. |
| 2013/0023988 A1 | 1/2013 | Sinnott et al. |
| 2013/0090731 A1 | 4/2013 | Walker |
| 2013/0096677 A1 | 4/2013 | Myers et al. |
| 2015/0150616 A1 | 6/2015 | Sharkey et al. |

OTHER PUBLICATIONS

U.S. Pat. No. 8,523,94; Apr. 30, 1907; Moses.

* cited by examiner

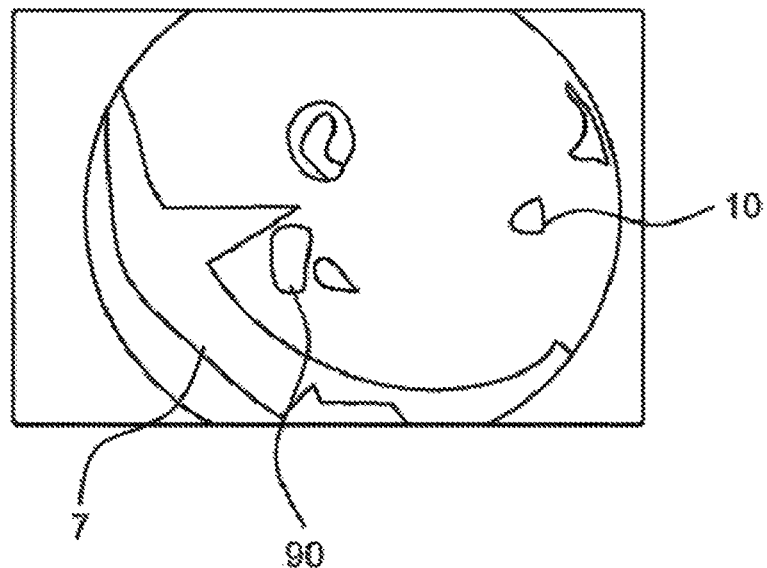
FIG. 8
PRIOR ART
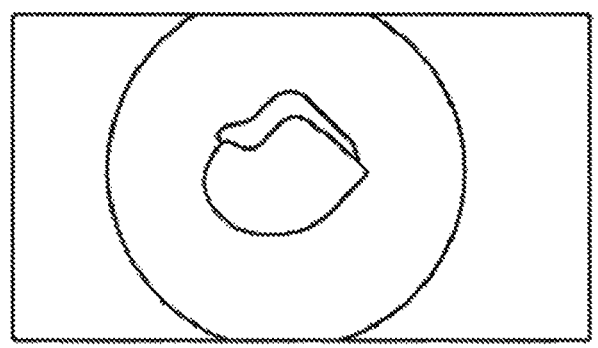
FIG. 9
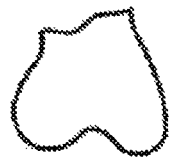      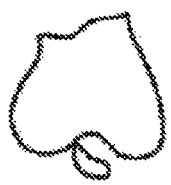
FIG. 9A           FIG. 9B           FIG. 9C

SYSTEM AND TECHNIQUE FOR ACCESSING EXTRA ARTICULAR LESIONS OR ABNORMALITIES OR INTRA OSSEOUS LESIONS OR BONE MARROW LESIONS

RELATED APPLICATIONS

This application is a continuation in part of co-pending U.S. application Ser. No. 16/118,750 filed on Aug. 31, 2018 which is a continuation in part of U.S. application Ser. No. 15/889,883 filed on Feb. 6, 2018, now U.S. Pat. No. 10,441,368 which is a division of U.S. application Ser. No. 15/265,178 filed on Sep. 14, 2016, now U.S. Pat. No. 9,925,010 issued on Mar. 27, 2018, which is a continuation in part of U.S. application Ser. No. 15/080,980 filed on Mar. 25, 2016, now U.S. Pat. No. 10,064,633 which is a continuation of U.S. application Ser. No. 15/080,947 filed on Mar. 25, 2016, now U.S. Pat. No. 10,064,632 entitled, "A System And Technique For Accessing Extra Articular Lesions Or Abnormalities Or Intra Osseous Lesions Or Bone Marrow Lesions" which claims priority from provisional application 62/297,478 filed on Feb. 19, 2016 entitled, "System And Technique For Accessing Extra Articular Lesions Or Abnormalities Or Intra Osseous Lesions Or Bone Marrow Lesions".

FIELD OF THE INVENTION

The present invention relates to the field of addressing lesions of bone marrow. A system and technique for accessing extra articular lesions or abnormalities or intra osseous lesions or bone marrow lesions is taught. The system and technique to define a virtual path and access to an extra articular osseous lesion through intra articular localization.

BACKGROUND OF THE INVENTION

Surgical procedures to repair bone defects such as lesions or abnormalities typically involve scooping out the damaged tissue material. One such procedure is called curettage. In these procedures, the bone is removed or opened to provide access to the lesion or cancerous tumor. This effectively weakens the bone structure because not only has the damaged tissue been removed, but also some of the load bearing solid bone structure. This is particularly problematic in the spine, the knees and the shoulder and articulating joints.

Ideally the surgeon would prefer to attack the problematic tissue without damaging the surrounding load bearing bone tissue. This is particularly difficult, however, because the damaged tissue material to be removed is hidden behind the joint. The current state of the art does not allow for accessing as well as addressing lesions of bone distant to the entry point of the localizing site.

The presently available systems and techniques do not adequately address this concern. The present invention described below provides an improved technique to remove the lesion, tumor or other abnormality without damaging the outer joint bone structure, and the surrounding cartilage, and soft tissue. This enables the healing and functionality of the repaired joint to be faster and far less painful.

Definitions

Bone cement: The bone cement PMMA (polymethylmethyacrylate) starts out as a liquid and hardens over time. It can be put into a hole in the bone in liquid form. As PMMA hardens, it gives off a lot of heat. The heat helps kill any remaining tumor cells. This allows PMMA to be used without cryosurgery for some types of bone tumors.

Bone Lesions: Various disorders can damage bones and result in bone lesions. Symptoms include bone pain or tenderness, and the injury can only be seen using special imaging tests. Bone lesions are abnormal areas of bone typically identified using an X-ray or MRI. Lucent bone lesions are caused by rapidly progressing bone injuries. Sclerotic lesions are bone injuries that develop more slowly, which allows the bone to attempt to wall off the damaged bone tissue. Bone lesions typically have cancerous and non-cancerous causes.

Bone Marrow Lesions: (BMLs), common osteoarthritis-related magnetic resonance imaging findings, are associated with osteoarthritis progression and pain.

Curettage: In this procedure, the doctor scoops out the tumor from the bone without removing a section of the bone. This leaves a hole in the bone. In some cases, after most of the tumor has been removed, the surgeon will treat the nearby bone tissue to kill any remaining tumor cells. This can be done with cryosurgery or by using bone cement.

Cryosurgery: For this treatment, liquid nitrogen is poured into the hole that is left in the bone after the tumor was removed. This extremely cold material kills tumor cells by freezing them. This treatment is also called cryotherapy. After cryosurgery, the hole in the bone can be filled by bone grafts or by bone cement.

Osteoarthritis: is the most common form of arthritis, affecting millions of people worldwide. It occurs when the protective cartilage on the ends of your bones wears down over time.

Osteochondritis dissecans: (OCD or OD) is a joint disorder in which cracks form in the articular cartilage and the underlying subchondral bone. OCD usually causes pain and swelling of the affected joint which catches and locks during movement. OCD is caused by blood deprivation in the subchondral bone. This loss of blood flow causes the subchondral bone to die in a process called avascular necrosis. The bone is then reabsorbed by the body, leaving the articular cartilage it supported prone to damage. The result is fragmentation (dissection) of both cartilage and bone, and the free movement of these bone and cartilage fragments within the joint space, causing pain and further damage. OCD can be difficult to diagnose because these symptoms are found with other diseases. However, the disease can be confirmed by X-rays, computed tomography (CT) or magnetic resonance imaging (MRI) scans.

Subchondral bone: bone located beneath or below the cartilage.

SUMMARY OF THE INVENTION

An improved low cost, preferably disposable instrument guide adapted to carry an access instrument used in accessing a compromised portion of a bone structure has a single piece guide body. The guide body has a first referencing arm and second referencing arm. The first referencing arm has a first end portion, wherein the first end portion of the first referencing arm has a reference structure integral therewith and wherein the reference structure defines a virtual axis. The second referencing arm is integral to the first reference arm and has at least one guide opening with a guide axis extending to intersect the virtual axis. The at least one guide opening is located at a fixed angle on the second referencing arm.

The second referencing arm has a portion in proximity to the first referencing arm configured to offset the intersection of the guide axis relative to the virtual axis by a fixed distance. The second arm has the fixed angle θ of one of the at least one guide openings set at 60 degrees, or 45 degrees or 50 degrees.

In one embodiment, the second arm has the fixed angle θ of a plurality of the at least one guide openings set at 10 degree increments. The offset can be set at a fixed distance between 0 to 5 cm or 1 cm to 5 cm.

The instrument guide can further have a guide sleeve configured to fit in one of the guide openings, the guide sleeve being coaxially aligned with the guide axis and can be configured to abut the patient at the location for an entry access. The sleeve in combination with the referencing structure abutting the patient along the virtual axis is configured to position and constrain the guide body as an access instrument passing through the guide sleeve forms an entry access passage to the compromised bone structure. Preferably, the guide sleeve tightly or snugly fits into the guide opening to fix a length between the patient and the guide body.

The instrument guide can further include an access instrument with graduations along a shank to establish a depth of an entry access passage into the compromised portion of the bone structure. The access instrument is configured to pass through one of the guide openings coaxially aligned with the guide axis.

A kit of instrument guides adapted to carry an access instrument used in accessing a compromised portion of a bone structure includes the plurality of guide bodies. Each guide body has a distinct angle θ for the guide opening and a distinct offset $D_O$ at a fixed distance, the kit providing guide openings between 0 and 90 degrees, more preferably 30 to 60 degrees and offsets between 0 and 5 cm, more preferably 1 to 5 cm.

In one embodiment, the kit of instrument guides has each guide body having a distinct angle of one of 30, 40, 45, 50 and 60 degrees. The kit of instrument guides also has guides wherein each guide body has a fixed offset of one of 0, 1, 2, 3, 4 or 5 cm. Each guide body of a kit can have a plurality of guide openings set at distinct angles θ between 0 and 90 degrees and each guide body has a distinct fixed offset $D_O$ relative to the other guide bodies of the kit. The kit further can include a guide sleeve configured to fit in one of the guide openings. The guide sleeve is configured to abut the patient at the location for an entry access, and in combination the referencing structure abutting the patient along the virtual axis is configured to position and constrain the guide body as an access instrument passing through the guide sleeve forming the entry access passage to the compromised bone structure.

The kit can further include an access instrument with graduations along a shank to establish a depth of an entry access passage into the compromised portion of the bone structure. The access instrument is configured to pass through one of the guide openings coaxially aligned with the guide axis.

The above-mentioned instrument guide allows for a unique method of treating a compromised portion of a bone structure. The method having the steps of: determining a reference location on an exterior surface of the bone structure defining a virtual axis extending through a target location adjacent to or within the compromised portion of the bone structure; determining an offset distance along the virtual axis from the reference location to the target location; determining an access axis extending through the bone structure at a location remote from the reference location and intersecting the target location, wherein the access axis extends through the virtual axis at a position defined by the offset distance; and forming, at least partially to the target location, an access passage along the access axis from the exterior surface of the bone structure using an access instrument, wherein said forming of the access passage includes mechanically constraining the access instrument relative to the reference location during said forming of the access passage.

Determining the offset distance can include imaging, prior to said forming of the access passage, a mass of the bone structure to identify information characterizing a distance between the target location relative and the reference location. The mechanically constraining the access instrument relative to the reference location includes engaging the access instrument with an instrument guide that is adapted to maintaining the access instrument at a fixed distance relative to the reference location and in a fixed angular orientation relative to the virtual axis. The forming the access passage includes arthroscopically viewing the exterior surface of the bone structure during said forming of the access passage and using said arthroscopic viewing of the exterior surface of the bone structure to maintain a reference structure of the instrument guide in contact with the exterior surface of the bone structure at the reference location thereof. Determining of the access axis includes determining an angular orientation of the access axis relative to the virtual axis and selecting a guide having a guide opening and guide axis aligned at an angle θ to the angular orientation of the access axis.

The method wherein: said forming the access axis is performed using an instrument guide; and said mechanically constraining the access instrument relative to the reference location includes: engaging the access instrument with the instrument guide; engaging a reference structure of the instrument guide with the reference location on the exterior surface of the bone structure; and using the instrument guide to manually manipulate an orientation of the instrument guide such that the virtual axis and the access axis both extend through the target location.

The mechanically constraining the access instrument relative to the reference location further includes: engaging the access instrument with a guide opening of the instrument guide jointly selecting a guide angle and an offset distance adjustor of the instrument guide such that a distance between the reference structure of the instrument guide and a point at which the access axis as defined by the selected guide opening is coaxial with an axis of the guide opening and intersects the virtual axis as defined by the reference structure of the instrument guide is the same as the fixed offset distance. The access axis extends through the virtual axis at a position defined by the offset distance.

The instrument guide is adapted to maintaining the access instrument at a fixed distance relative to the reference location and in a fixed angular orientation relative to the virtual axis. Forming the access passage includes arthroscopically viewing the exterior surface of the bone structure during said forming of the access passage and using said arthroscopic viewing of the exterior surface of the bone structure to maintain the reference structure of the instrument guide in contact with the exterior surface of the bone structure at the reference location thereof. The bone structure includes subchondral bone and cartilage supported thereby; the reference location on the exterior surface of the bone structure is at an exposed surface of the cartilage within an appendage articulation joint; said engaging the reference structure of the instrument guide with the reference location on the exterior surface of the bone structure consists of engaging the reference structure with the exposed surface of the cartilage. Forming the access passage includes arthroscopically viewing the exposed surface of the cartilage supported by the subchondral bone during said forming of the access passage. Mechanically constraining the access instrument relative to the reference location includes using said arthroscopic viewing of the exposed surface of the cartilage to maintain engagement of the reference structure of the instrument guide at the reference location.

The method preferably has said forming the access axis being performed using an instrument guide. Said mechanically constraining the access instrument relative to the reference location includes: engaging the access instrument with a guide opening of the instrument guide; and jointly selecting the angular orientation of the guide opening and a fixed offset distance of the instrument guide such that a distance between the reference structure of the instrument guide and a point at which the access axis as defined by the angular orientation of the guide opening intersects the virtual axis as defined by the reference structure of the instrument guide is the same as the fixed offset distance; and said forming the access passage includes manipulating an orientation of the instrument guide such that the virtual axis and the access axis both extend through the target location while maintaining a reference structure of the instrument guide with the reference location on the exterior surface of the bone structure.

The access axis extends coincidental with a longitudinal axis of the guide opening; and said mechanically constraining the access instrument relative to the reference location includes engaging a portion of the access instrument within the guide opening. The instrument guide that is adapted to maintaining the access instrument at a fixed distance relative to the reference location and in a fixed angular orientation relative to the virtual axis. Forming the access passage includes arthroscopically viewing the exterior surface of the bone structure during said forming of the access passage and using said arthroscopic viewing of the exterior surface of the bone structure to maintain the reference structure of the instrument guide in contact with the exterior surface of the bone structure at the reference location thereof.

The bone structure includes subchondral bone and cartilage supported thereby; the reference location on the exterior surface of the bone structure is at an exposed surface of the cartilage within an appendage articulation joint. Said engaging the reference structure of the instrument guide with the reference location on the exterior surface of the bone structure consists of engaging the reference structure with the exposed surface of the cartilage; said arthroscopically viewing the exterior surface of the bone structure includes arthroscopically viewing the exposed surface of the cartilage supported by the subchondral bone; and said mechanically constraining the access instrument relative to the reference location includes using said arthroscopic viewing of the exposed surface of the cartilage to maintain engagement of the reference structure of the instrument guide at the reference location.

BRIEF DESCRIPTION OF THE DRAWINGS

The invention will be described by way of example and with reference to the accompanying drawings in which:

FIG. 8 is an example of a prior art lesion fixation.

FIG. 9 shows a bone lesion.

FIGS. 9A, 9B and 9C show diagrammatically how the lesion can be separated exposing the bone marrow.

DETAILED DESCRIPTION OF THE INVENTION

The present invention has a variety of embodiments showing various instrument guides with an array of adjustment capabilities and features as illustrated in FIGS. 1-32C. In the present invention illustrated in FIGS. 33-35, an instrument guide 20' employs a guide component or guide body 21 with a fixed angular orientation θ and a fixed offset distance $D_O$.

Ideally, this simplified design of the instrument guide 20' allows the device to be made as a single piece guide body 21 that can be made of stainless steel for sterilization and reused or alternatively a molded or 3D printed device made of a thermoplastic material that can be sterilized and used once and disposed of.

In the case of the 3D printed device, the guide body 21 can be custom fabricated using imaging of a joint or compromised bone structure in need of repair and the device custom fitted to the patient's body structure allowing the derived virtual axis and access axis to be established so the guide referencing structure and guide opening axis can be fixed at the surgeon's choice based on the patient's exact anatomical features.

In the case of pre-molded guide bodies 21, a variety of sizes can be made with fixed guide openings. The instrument guide 20' can be provided as a kit 100 with several guide bodies 21 with fixed angles and offsets from which the surgeon can select the best one to access a bone abnormality.

Figure 36:
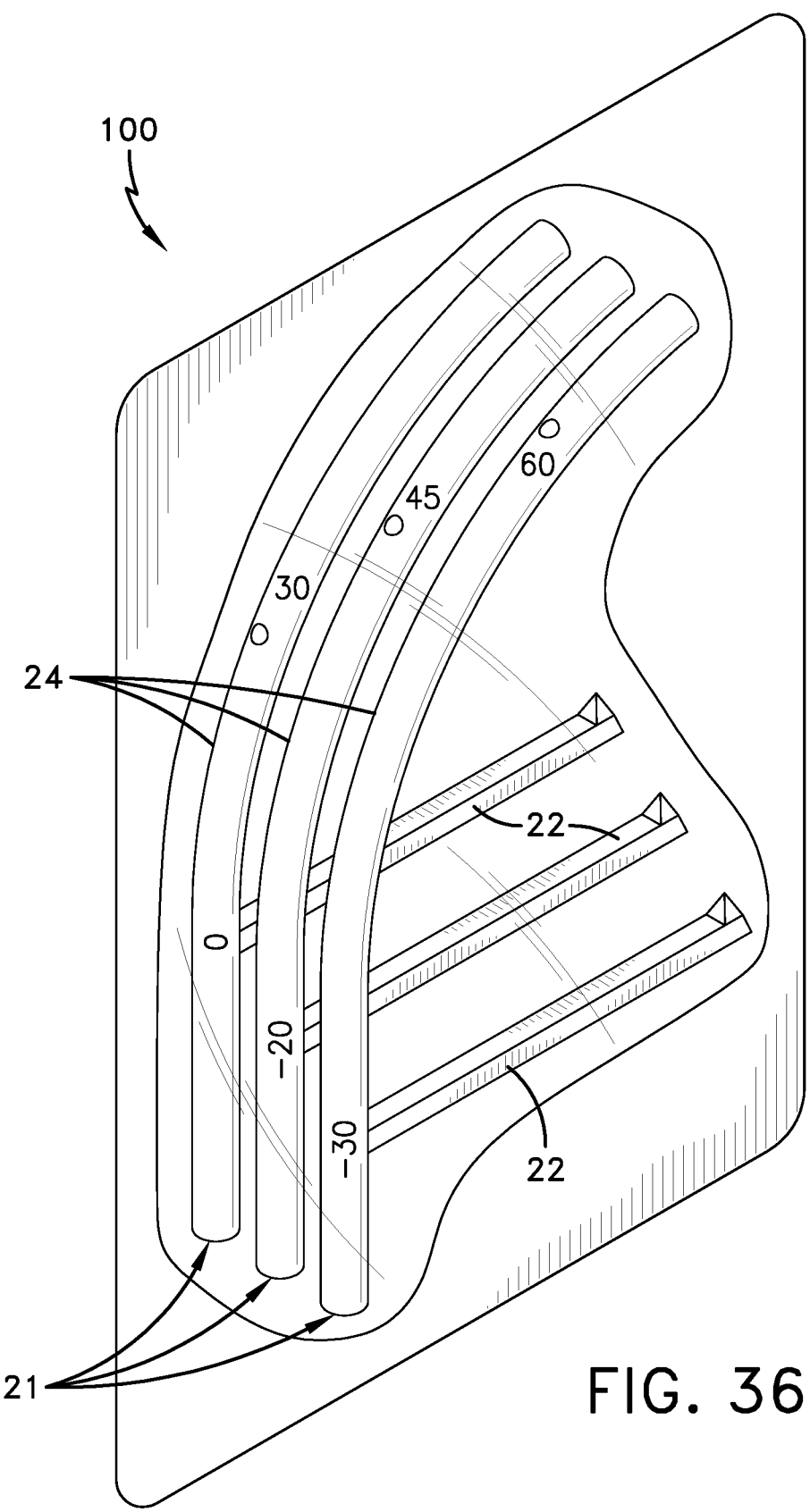
FIG. 36 is an illustration of a plurality of the guide bodies of the instrument guide of the present invention packaged into a kit.

As shown in FIG. 36, an exemplary kit 100 of several of the guide bodies 21 of the instrument guide 20' can be assembled into a package containing, for example, guide bodies 21 having distinct offsets $D_O$. As shown, three guide bodies 21 have different offsets $D_O$ of 0 mm, 20 mm and 30 mm, respectively. In this illustration, each guide body 21 in kit 100 has the guide angle θ provided at three openings 30 degrees, 45 degrees and 60 degrees. Other combinations of guide bodies 21 can be assembled into other kits of other combinations of offsets and angles.

Figure 33:
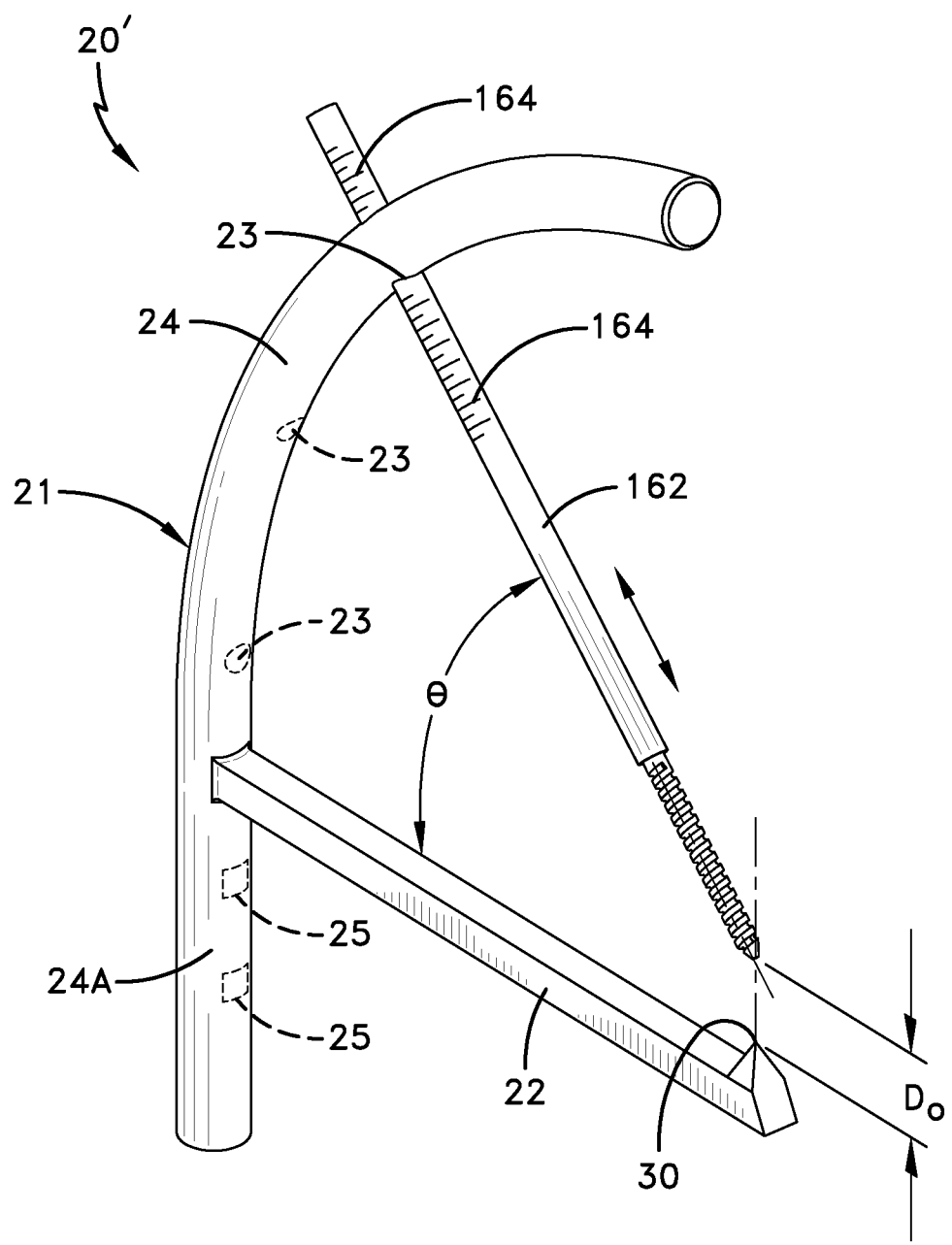
FIG. 33 is a forward facing perspective view of the present invention instrument guide of an embodiment with a first and second arm having a fixed angle and fixed offset set distance.
Figure 34:
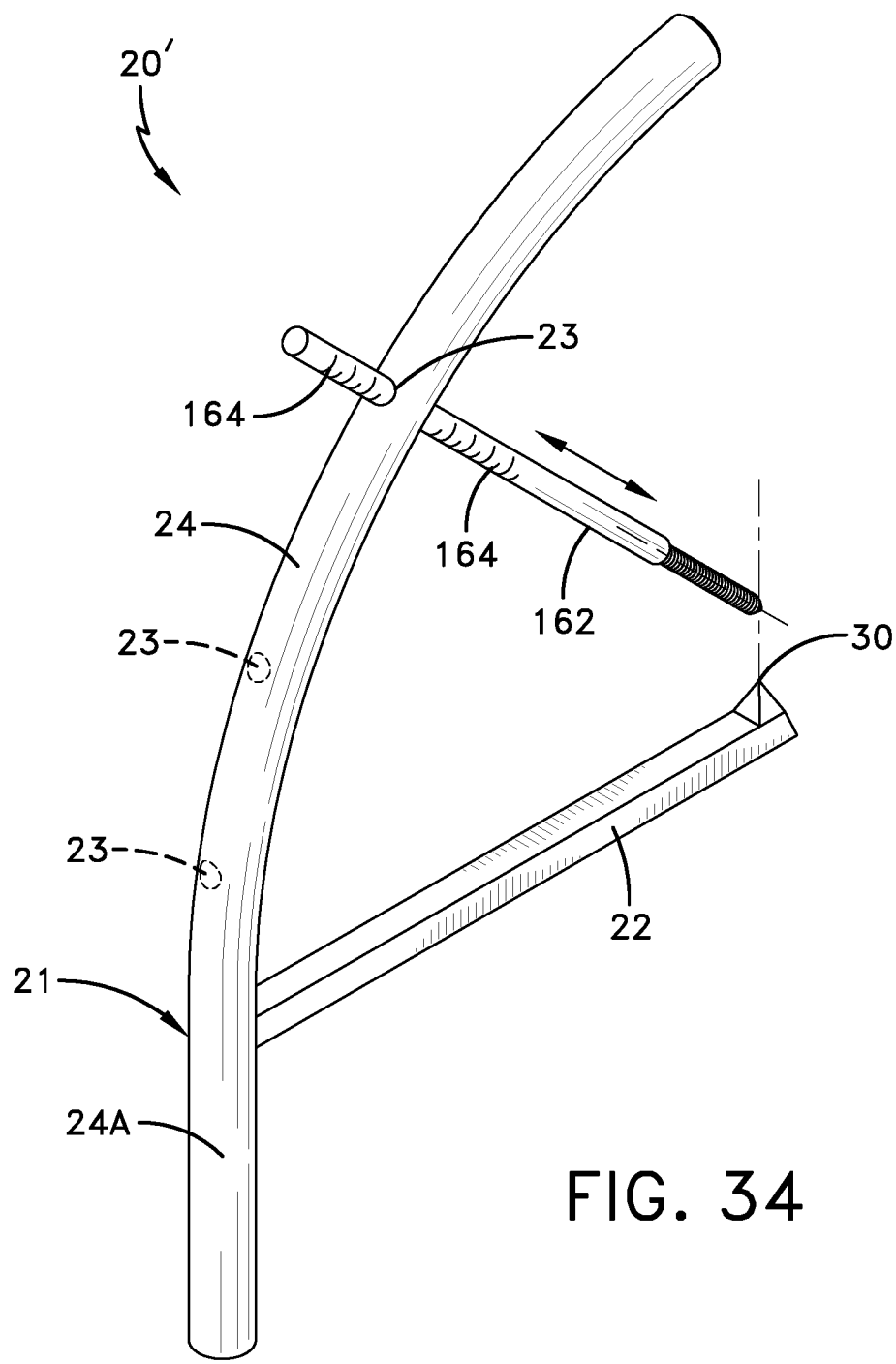
FIG. 34 is a rearward facing perspective view of the instrument guide of FIG. 33.
Figure 35:
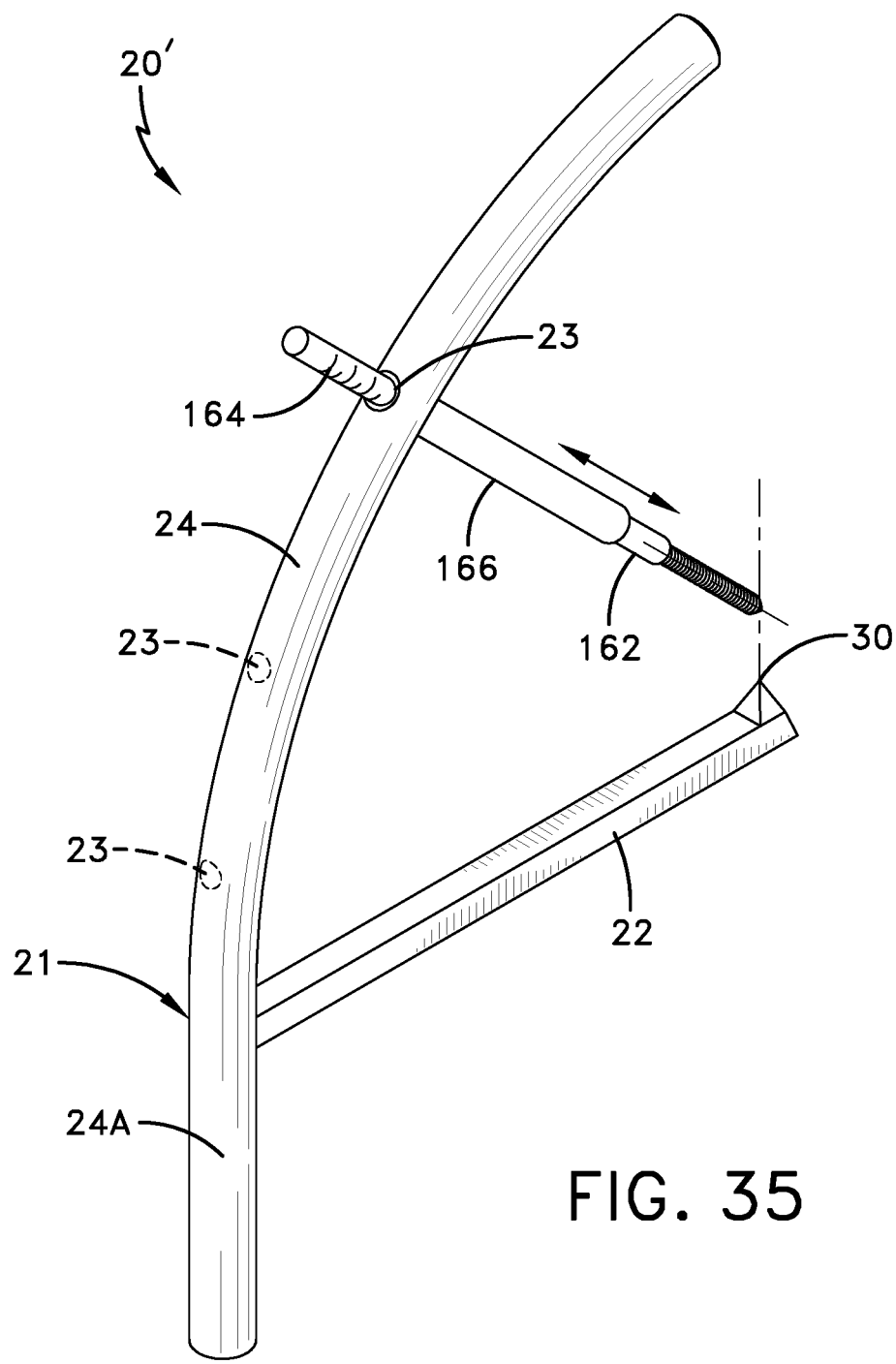
FIG. 35 is a rearward facing perspective view of the instrument guide of FIGS. 33 and 35 with a guide sleeve.

As shown in FIGS. 33 and 34, a representative instrument guide 20' is shown. The instrument guide 20' has a guide body 21 made as a one-piece device having a first referencing arm 22 and a second referencing arm 24. The first referencing arm 22 has a first end portion with a localizing pinning member or reference structure 30 integral therewith. The reference structure 30 defines a virtual axis. As shown in FIGS. 33-35, the virtual access axis is parallel to the straight portion 24A of the second referencing arm 24 and extends from the reference structure 30.

The second referencing arm 24 is integral to the first referencing arm 22. As shown, the second referencing arm 24 has a curved or arcuate shaped portion extending to a straight portion 24A. The first referencing arm 22 projects from the straight portion 24A as shown. The location at this position defines an offset feature which is a fixed distance $D_O$ at or below an intersection of an access angle intersecting the virtual axis shown extending from the reference structure 30. The guide body 21 can be made at any offset distance between 0 to 5 cm or more. The phantom or dashed lines 25 illustrate optional locations of the first referencing arm 22 to project from the straight portion 24A.

As shown, the first referencing arm 22 is illustrated as extending straight out from the second referencing arm straight portion 24A with the angle θ showing an access instrument 162 held at the fixed angle θ by a guide opening 23. The first referencing arm 22 while shown as a straight member could be curved or multi-curved with a combination of alternative shapes employing straight and now straight sections as long as the reference structure 30 is set at a desired offset distance. The use of a straight arm is believed helpful as the surgeon holds the device he can easily visualize the offset of the particular instrument guide 20'. The guide opening 23 has a guide axis that is coaxially aligned with the access axis such that the access instrument 162 has a longitudinal angle θ that is coaxially aligned. As shown, the access instrument 162 can be a drill having a fluted drill end extending distally and a shank of a diameter to snugly fit in the guide opening 23 so as to maintain the angle θ without wobbling. As shown, a graduated scale 164 extends along the shank to aid the surgeon to see the depth of bone penetration during the step of forming the access passage into the bone. The access instrument 162 is free to slide axially in and out of the guide opening 23 as well as to rotate therein to create the access passage to the compromised portion of the bone.

The guide opening 23 can be positioned anywhere along the curved or arcuate portion of the second referencing arm 24. As illustrated, the resultant angle θ is set at 60 degrees, any angle θ could be made between 0 and 90 degrees, more preferably for this procedure between 30 and 60 degrees is more ideal.

Figure 28:
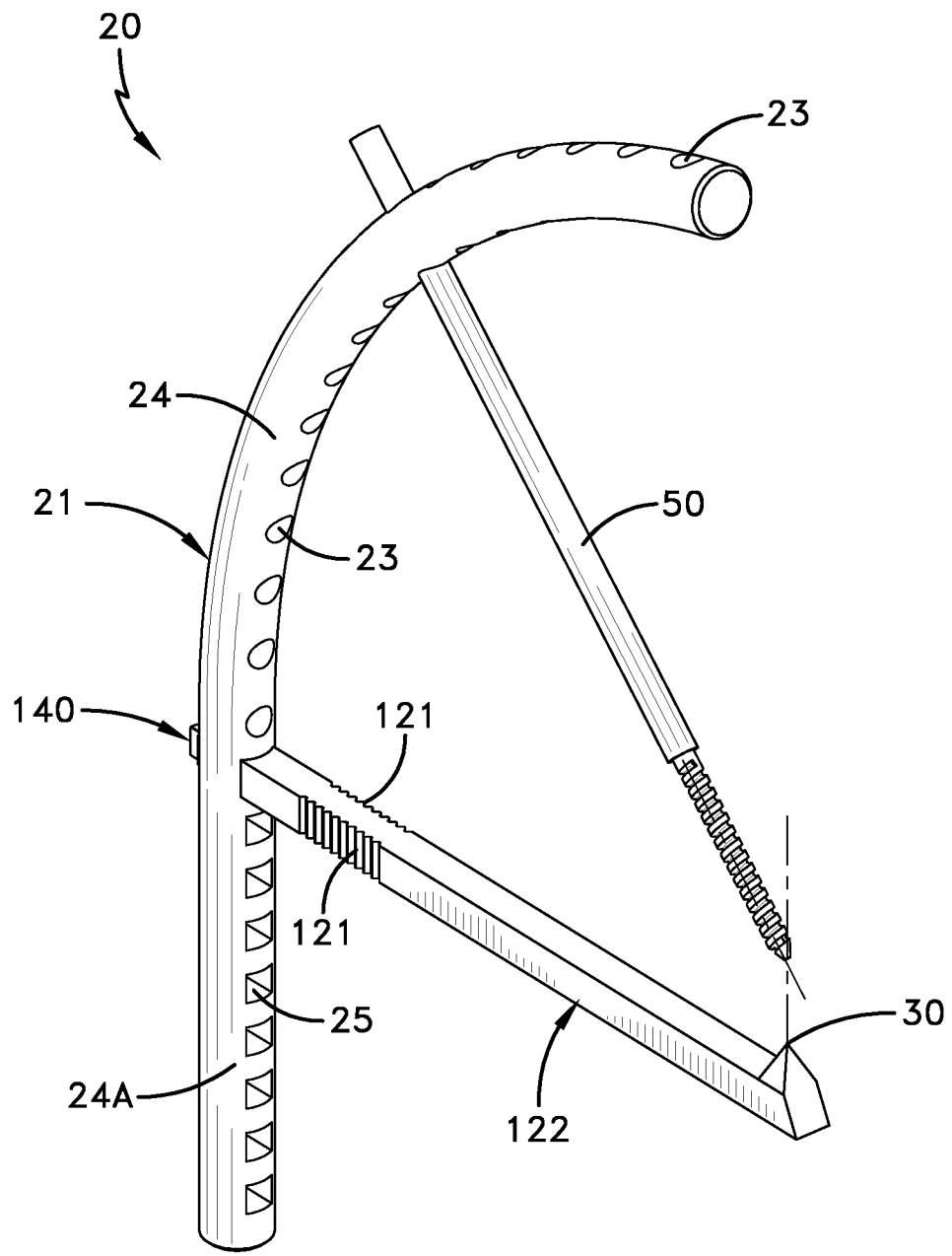
FIG. 28 is a first perspective view of a fourth embodiment of the present invention showing a system for accessing extra articular lesions or abnormalities or intra articular lesions or abnormalities or bone marrow lesions or bone marrow lesions or all using intra articular localization.

The curved portion of the second referencing arm 24 could be made with a plurality of fixed openings similar to that device as shown in FIG. 28. In such a case, 30 degrees or 45 degrees or 50 degrees or 60 degrees or guide openings 23 set at 10 degree increments could be provided.

With reference to FIG. 35, an alternative feature is shown where the access instrument 162 is put in a guide sleeve 166 configured to fit in the guide hole 23. The guide sleeve 166 allows the access instrument 162 to slide in and out as well as rotate to form the access passage. The guide sleeve 166 can be configured to rest on the location of the entry for the access passage and provide a stabilizing feature for the surgeon holding the referencing structure 30 on the bone and the sleeve 166. Alternatively, the access instrument 162 itself can provide a second point of contact for constraining the guide body 21 during the formation of an access passage.

This improved instrument guide 20' performs all the methods of accessing a compromised portion of a bone as those devices explained hereinafter, but at fixed access angles and fixed offsets, if any offset is desired. The access instrument guided along the guide axis of the guide opening 23 coaligned access can penetrate to the intersection of the virtual access or through and past the intersection or stop short of the intersection at the surgeon's choice. The surgeon can image the compromised bone, plan the ideal path for the access passage to be formed and then select an instrument guide 20' with the best offset distance and access angle θ to achieve the result. Alternatively, the guide body 21 can be 3D printed to the exact access angle θ and offset $D_O$. The advantages of the present invention are many First, the instrument guide 20' has a simplicity and elegance of design. Second, the surgeon needs to make no adjustments to the device, he simply selects or makes the guide body 21 best suited for the task. Third, the guide body 21 being made as a one piece structure makes it ideal for injection molding or 3D printing. Fourth, the cost to manufacture can be significantly lower than adjustable devices while still providing the capabilities of the more expensive adjustable multi-piece devices. We refer the reader back to the summary of the invention for a detailed description of the techniques and methods for using the instrument guide 20'.

The following detailed description of the adjustable instruments is provided with the understanding that the devices in FIGS. 1-32C once adjusted to the desired angle θ and offset distance DO will perform or provide the exact function of the instrument guide 20'. With the reader's understanding of this fact, all the techniques explained hereinafter are usable with this instrument guide 20'.

With reference to FIGS. 1-7, a first embodiment of the present invention is illustrated. The first embodiment of the present invention provides for a pinning member access 11, which is the first entry access, to be created through the cartilage 5 and subchondral bone 7 using a guide component 21 which further enables a localizing pinning member 30 to penetrate into the first entry access 11 and by utilizing the guide component 21 allows for a precise location for a second entry access 12 location to be created. The guide component 21 consists of first arm 22 and second arm 24 including the straight portion 24A.

Figure 10:
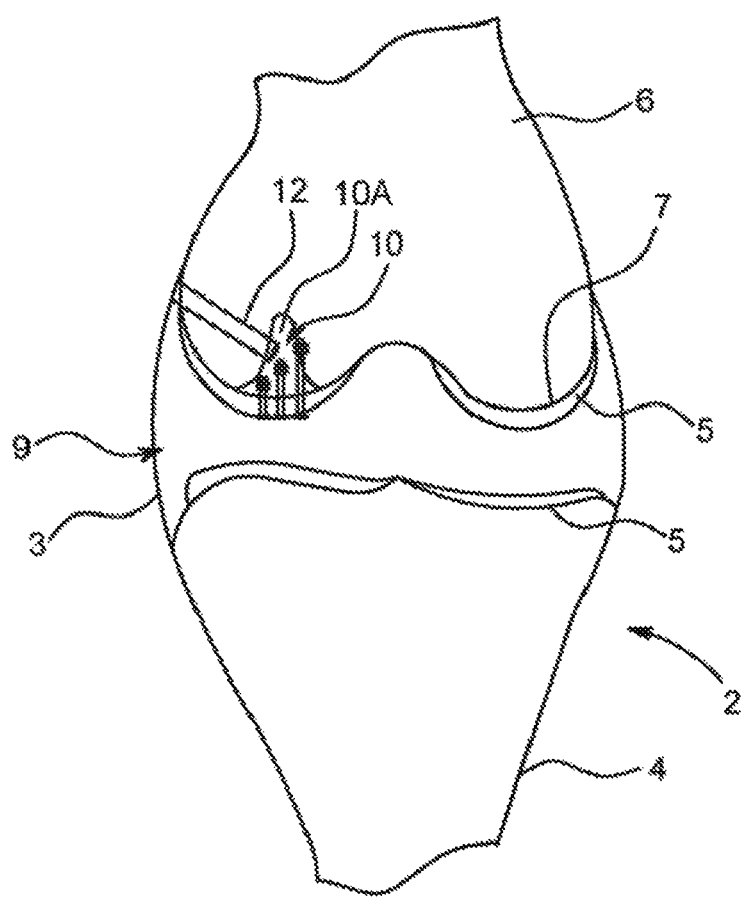
FIG. 10 is a joint showing fixation anchors or pins pre-set through the subchondral bone and cartilage with the second access extending toward the end of the pins.
Figure 11:
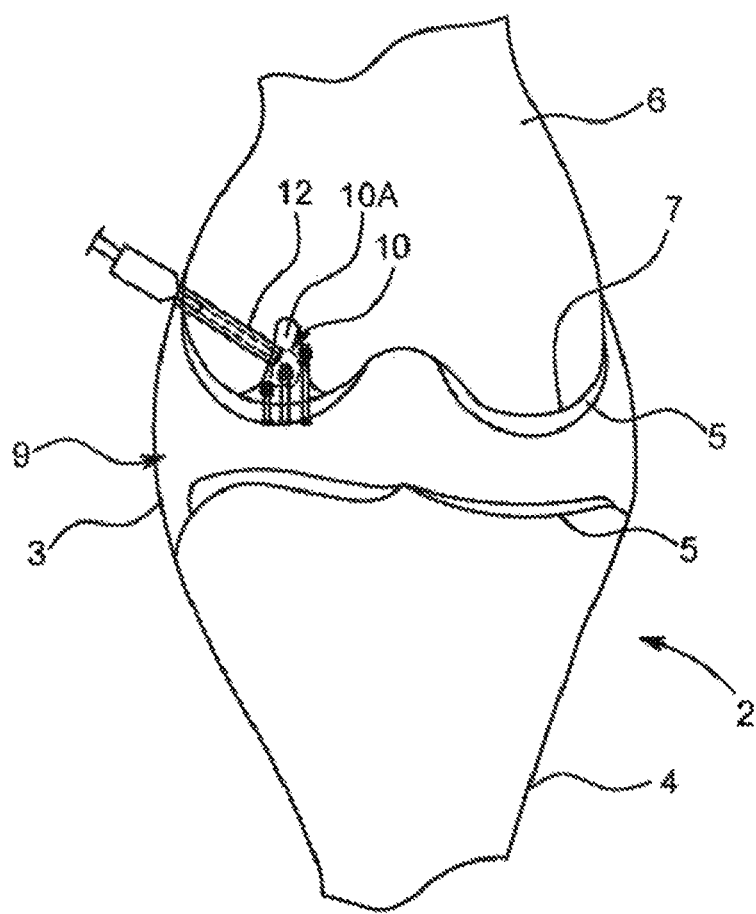
FIG. 11 shows how a bone cement can be injected with a filled syringe into the lesion or abnormality cavity to encapsulate the pins or bone anchors.
Figure 12:
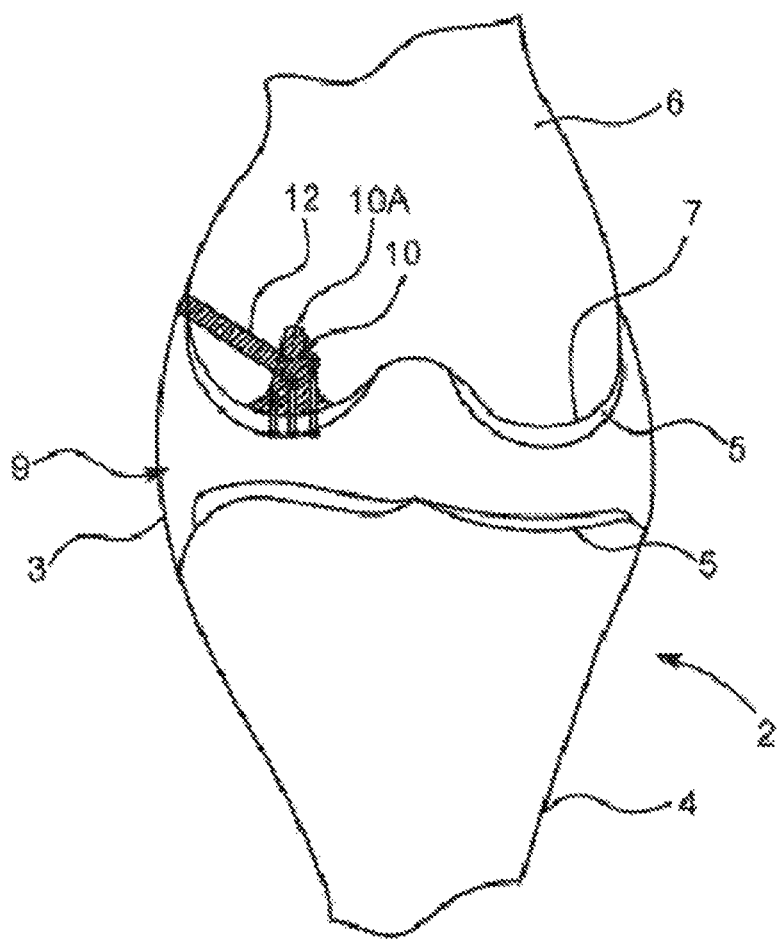
FIG. 12 shows the repair structurally cemented and fully supported lesion or abnormality repair.
Figure 13:
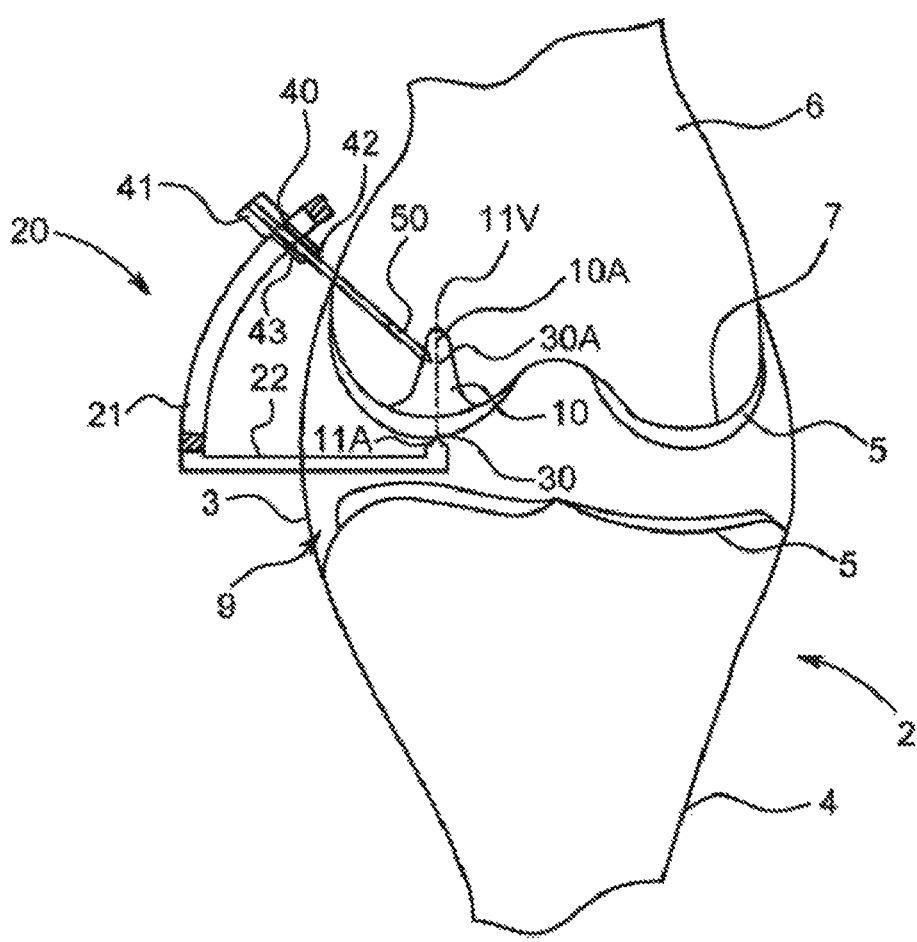
FIG. 13 shows a second embodiment of the invention wherein a virtual pathway is used when positioning the localizing pinning member which does not penetrate through subchondral bone or the cartilage as illustrated, but rather is located on the cartilage.

With reference to FIGS. 10-12, pins or anchoring devices 90 can be inserted through cartilage 5 and subchondral bone 7 into a lesion 10 or abnormality and the creation of a second entry access 12 location provides a means through which the pins or anchors 90 can be structurally supported by the addition of bone cement 62. A syringe 60 can be placed into the second entry access 12 through which the bone cement 62 or other fixing agents can be syringed through the second entry access portal 12 into the lesion 10 to encapsulate the bone screw 90, as shown in FIG. 11. In FIG. 12, the residual cement 62 that is packed into the cavity where the abnormality or lesion was and the second entry access is filled as illustrated sealing the opening wherein the anchors 90 are firmly secured. This structurally supporting cementing of the pins or anchors 90 works equally well with the second embodiment of the present invention wherein the entry access 12 is used to fill the lesion cavity 10, 10A and seal the angled tunnel or track entry access 12 to support the pins or anchors 90.

With reference to FIGS. 13-18, the second embodiment of the invention is illustrated. This second embodiment is very similar to the first embodiment. However, the localizing pinning member 30 creates a virtual pathway 11V through the cartilage 5 and subchondral bone 7 without requiring a pinning member 30 entry access 11 whereby an entry access 12 can be created that intersects a line $L_1$ projected along the virtual pathway 11V from an end of the localizing pinning member 30 in such a way that the entry access $L_2$ when projected along a track will intersect at a target location along the virtual pathway 11V. In this embodiment, as will be discussed later, the subchondral bone and cartilage need not be penetrated and no pinning member entry access opening is created. However, the virtual pathway 11V is created projecting to a lesion allowing the surgeon to precisely direct and create one or more than one entry access portals or openings 12, 14 using the guide component 21 of the present invention.

Figure 1:
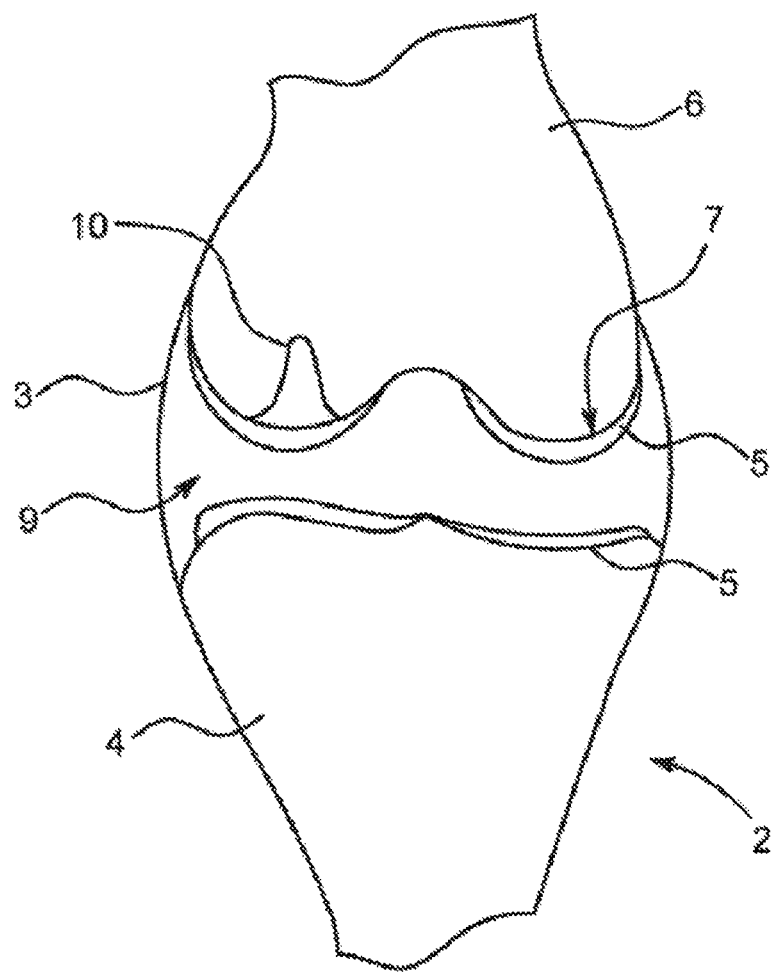
FIG. 1 shows a plan or frontal view of a relatively normal joint with the bone marrow lesion from osteochondritis dissecans with the femur above and the tibia below.

The present invention addresses lesions 10 of bone, as shown in FIG. 1, which may or may not be visualized arthroscopically. This could be in situations where the patient has intact articular cartilage 5, such as the situation with osteochondritis dissecans. The surgeon can tell where the lesion 10 is by probing. There can be situations dealing with osteoarthritis or other lesions of the bone marrow where the subchondral bone 7 is intact. In either case, the surgeon wants to be able to locate where the lesion 10 of the bone is that can't be visualized, it is essentially extra articular, it is within the bone. This could be termed a bone marrow lesion, but in this technique, the surgeon uses intra articular techniques to access the lesion.

The current art on this is very limited because generally it would be utilizing fluoroscopy or other means to vaguely localize where that lesion might be. Sometimes the lesion can't even be seen on fluoro. One may argue that a pin can be placed in through it, but there are no localizing techniques other than fluoro and imaging which have significant limitations.

Figure 2:
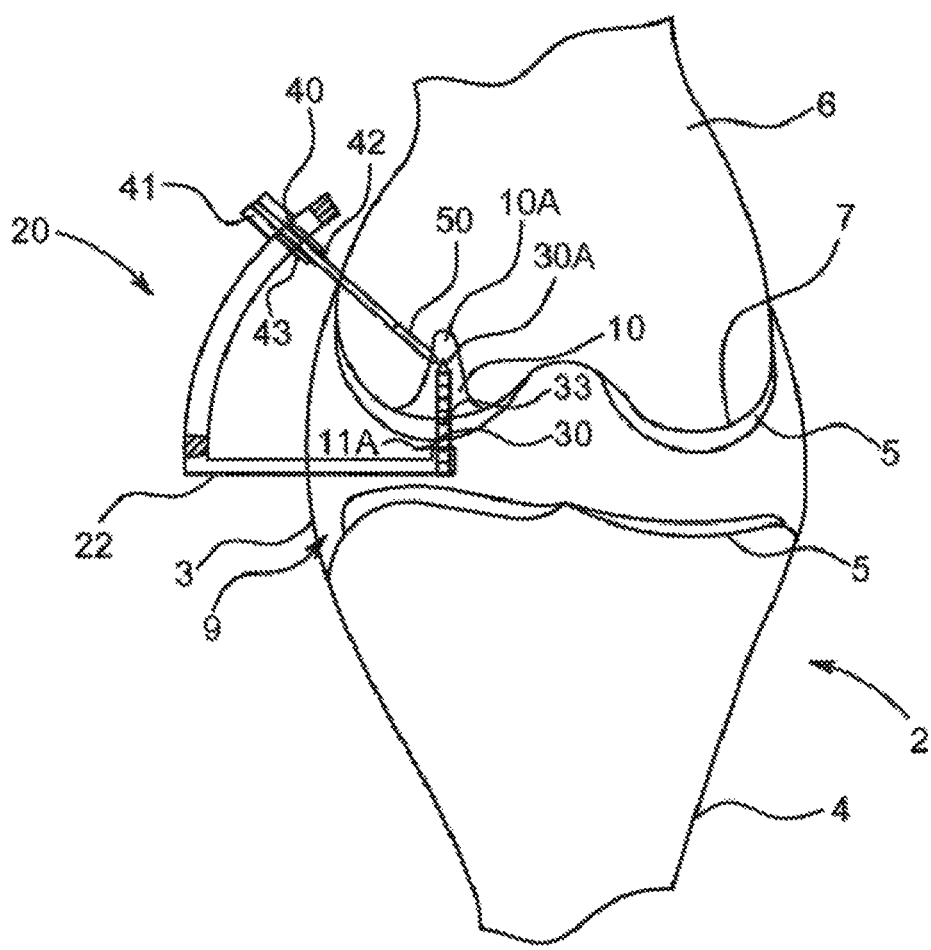
FIG. 2 shows the normal joint of FIG. 1 with the system of the present invention.
Figure 3:
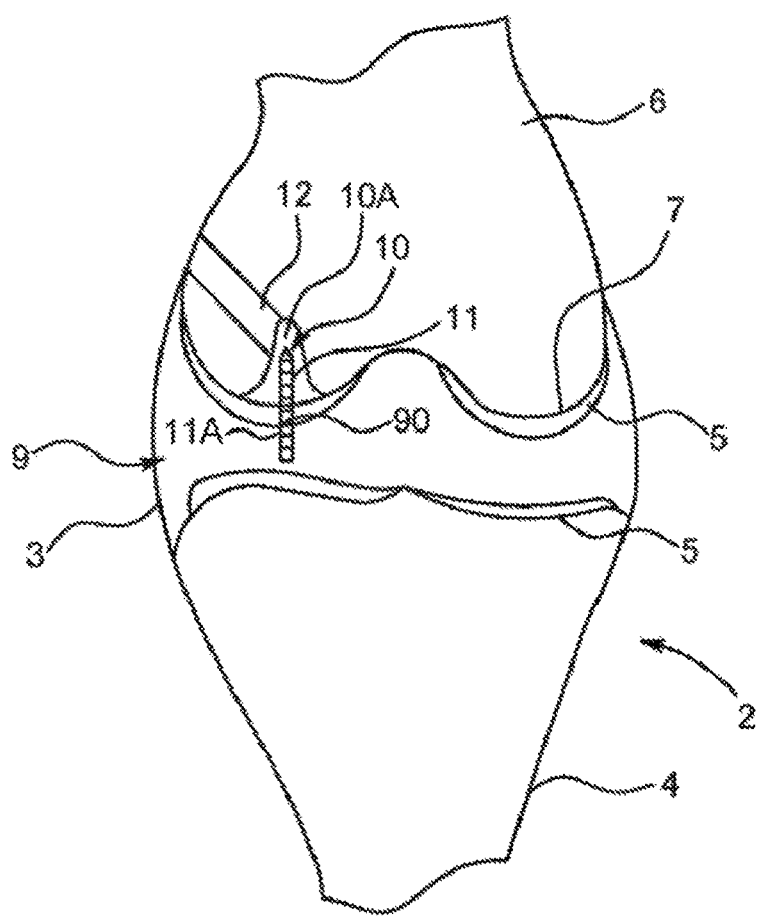
FIG. 3 demonstrates the normal joint with the first entry access and second entry access formed and the system device removed.
Figure 3A:
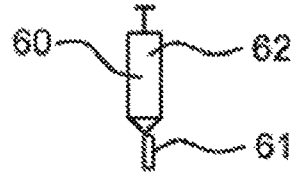
FIG. 3A is a plan view of an exemplary syringe filled with a bone putty or similar material for injection through the second entry access.
Figure 3B:
FIG. 3B is an exemplary camera or imaging scoping device for visualizing the lesion through the second entry access.

In the first embodiment of the present invention, as shown in FIG. 2, the provided device or system 20 of the present invention allows the surgeon to actually put a pinning member 30 into the lesion 10 through articular cartilage 5, or in a situation of the osteochondritis dissecans lesion, the surgeon can place the pinning member 30 through the subchondral bone 7 to address a bone marrow lesion 10. The surgeon applies a guide component 21 to that localizing pinning member 30. The guide component 21 has a movable guide 40 forming a system that allows for extra articular access to the end or point of the localizing pinning member 30 which is something that is not visualized, but rather is something within that bone marrow lesion 10 or within the bone at a point 10A distal from the intra articular visualized entry point 11A and access to it occurs from outside the joint 2. The surgeon could actually access it from even inside the joint 2, but coming from a different point or direction. And now by accessing the lesion 10 and removing the damaged tissue, the surgeon can introduce substances into it, such as bone mineral grafting, calcium phosphate, etc. or you can even put a camera system 70, as shown in FIG. 3B, through the second entry access track or portal 12 that was created to look at or modify the lesion 10 by putting different types of reamers 80, shown in FIG. 3C, into it and selected substances using a syringe 60 filled with a material 62 such as putty or bone allograft or bone cement, as shown in FIG. 3A. Then one can, after that has been done, put fixation pins 90 additionally into it from the intra articular utilizing the initial pinning member 30 access 11, one can put pins and fixation devices 90 around it to help further fix the lesion, as shown in FIG. 3.

The limitation of the prior art techniques is that they allow for no precise localization of lesions which cannot be seen. It may be argued that when one uses the prior art guide systems, the problem is that these create straight tracks. The prior art in line devices don't create angled tunnels, this inventive technique requires an angled tunnel to be created because the surgeon wants the extra articular point of entry to be somewhere remote from the pinning member 30 entry point 11A which is the intra articular localizing point 11A. The best way to do that is to create an angled tunnel or an angled track. If using the standard prior art in-line guides, with its exit point at the intra articular point coming in from outside in, one does not create an appropriate track and can actually violate that subchondral bone and the lesion. Furthermore, this does not provide an appropriate methodology for introducing substances in a sophisticated manner or in a precise manner. The present invention is a complete and different approach to it and introduces and provides an entirely new system of devices and instruments to be used for these purposes. Limitations of the prior art as mentioned before is there are no methodologies for addressing and accessing lesions one cannot see when one wants to visualize or repair remote from the initial entry localizing point. That is a big difference.

The present invention allows for precise localization of a lesion 10 and a way to access it while minimizing load bearing bone structure damage caused by the surgical repair by essentially leveraging the inventor's angled osteal tunnel concept of creating blind tunnels. In the first embodiment, the surgeon is now able to drill a hole 11 into subchondral bone 7 of the femur 6 and from another angled entry point create an access track or portal 12 so the tip of that pinning member 30 and the drill 50 extend along intersecting lines $L_1$ and $L_2$ so that the location 10A is triangulated. This allows for precise localization of the lesion 10 and access to it.

One example where this is most useful is to access the lesion 10 from within the joint 2 such as the knee joint 2. This is called intra-articular. The surgeon can drill a pinning member 30 from within the joint 2 into the bone even going through intact cartilage it necessary. Then, from coming outside of the joint 2 with another drill 50, he or she can then articulate to a blind spot or point 10A within bone knowing it is accurate based on the precision of the guide system 20 instruments. Often times, the lesion 10 being addressed maybe a cystic lesion. The surgeon can then introduce other reamers 80 into this second access portal 12, the reamer 80 is configured to expand at tip 82 once it gets to that desired lesion spot to clean this out. The removed lesion tissue forms a cavity which can then be filled with bone grafting material substance 62 through a cannula 61 that came in from outside of the joint 2. This technique uniquely allows for blind targeting a point or location 10A within bone. The invention in an earlier angled osteal tunneling technique, was for retrieving sutures. In this technique, the surgeon is using the angled tunnels as portals 12, 14 for delivering material 62 to that spot. Additionally, he can also place a camera 72 through one of the portals 14, see FIG. 7, which will then allow for him to directly visualize what is taking place within the lesion 10 using one portal 14 for the camera 72 and another portal 12 for instruments. As shown, the camera 72 is connected by a flexible cable or tube 71 to a display monitor 78 for real time viewing.

One of the best examples of utilization of this technique is in the case of osteochondritis dissecans. This is a serious lesion in children and young adults where the cartilage 5 can be intact within the joint 2, but the bone 7 behind it essentially cystic or a vascular. The surgeon knows where the lesion 10 is from looking inside the joint 2, but he can't access the dead bone without violating the cartilage 5. Hence, with this inventive technique, he simply drills up in through the intact cartilage to help stabilize it using the pinning member 30. Then coming from outside the joint 2 he can address the diseased bone, clean it out and put material 62 using the second entry access portal 12. He can then, from inside the joint 2, further stabilize the lesion 10.

There are a number of key points the inventor would like to emphasize regarding the present invention. First, the access to a bony lesion 10 from within a joint (intra-articular) or from outside the joint (extra articular) is greatly enhanced. The ability to use the tunnel portal tracks 12, 14 either for retrieval or for delivery of materials 62 is achieved. The ability to use the tracks 12, 14 to place cameras 72 and working instruments 80 to look inside of the bony lesions 10 is accomplished. The precise targeting of bony lesions 10 blindly using a technique of triangulation with the guide system 20 instruments or devices of the present system is available.

FIG. 1 shows a relatively normal joint 2 with the bone marrow lesion 10 from osteochondritis dissecans, as shown the joint 2 has the femur 6 above and the tibia 4 below. The figure outlines the articular cartilage 5 and right behind the cartilage is subchondral bone 7. Also drawn is the capsule 3, anything outside the capsule 3 is what is called extra articular; inside the capsule 3 is called intra articular space 9. The bone marrow lesion 10 which is hidden from view because it is behind that cartilage 5. It may be behind subchondral bone 7 in a situation where you have arthritis and don't actually have that cartilage over it. The point is one can't see the lesion 10 behind what they are looking at from the scope.

FIG. 2 shows how this would be addressed. The surgeon would put a pinning member 30 through the cartilage 5 and the subchondral bone 7 or just the subchondral bone 7 if there was no cartilage 5, so it actually goes into the bone marrow lesion 10. This pinning member 30 can go into it or it can go all the way through the lesion 10. Then, utilizing the guide system 20, coming from outside in a generally extra articular approach, but it may not be if it just comes in from a different direction to form a second or even more access portals 12, 14. In any event, these second and one or more additional portals 12, 14 do not go through the articular cartilage 5. The key is that the surgeon is accessing this lesion 10 within the bone from a safe area that doesn't damage the joint 2. The access doesn't damage the other anatomical structures; that is why he has to have the variability of a range of depth and the variability of a range of angles combined with the ability to rotate the guide component 21 around the axis of the pinning member 30. One can't have a fixed point of entry because that can be dangerous. This adjustment capability allows the surgeon to access the lesion 10 from a different location, generally an extra articular location, that's what's demonstrated how the guide 20 works on this example as shown in FIG. 2.

Figure 3C:
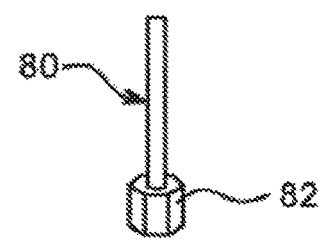
FIG. 3C is an example of an expandable reamer for cleaning the lesion material during repair through the second entry access.

FIG. 3 demonstrates what is done when you have that track formed on an angled osteal tunnel access portal 12. Once that separate track 12 is created, the surgeon can enlarge the track 12 with reamers 80, can put different types of reamers 80 in, which are small going in, then they expand once they get to the lesion 10, flip cutters, or other types that can be utilized in that situation. The surgeon can use the track or access portal 12, 14 to fill the cavity created when the lesion tissue is removed with different substances 62 including bone mineral matrices, stem cells, or can even put cameras 72 inside. As illustrated, a putty filled syringe 60, a camera system 70 or an expandable reamer 80 with tip end 82 can be used, as shown in FIGS. 3A, 3B and 3C respectively. Once filled in, these different substances can set, then the surgeon can go back into the joint 2 and can put multiple pins 90, and fixation devices 90 which can now be better fixed because there is some substance within the lesion 10 cavity which he can fix them to.

Figure 4:
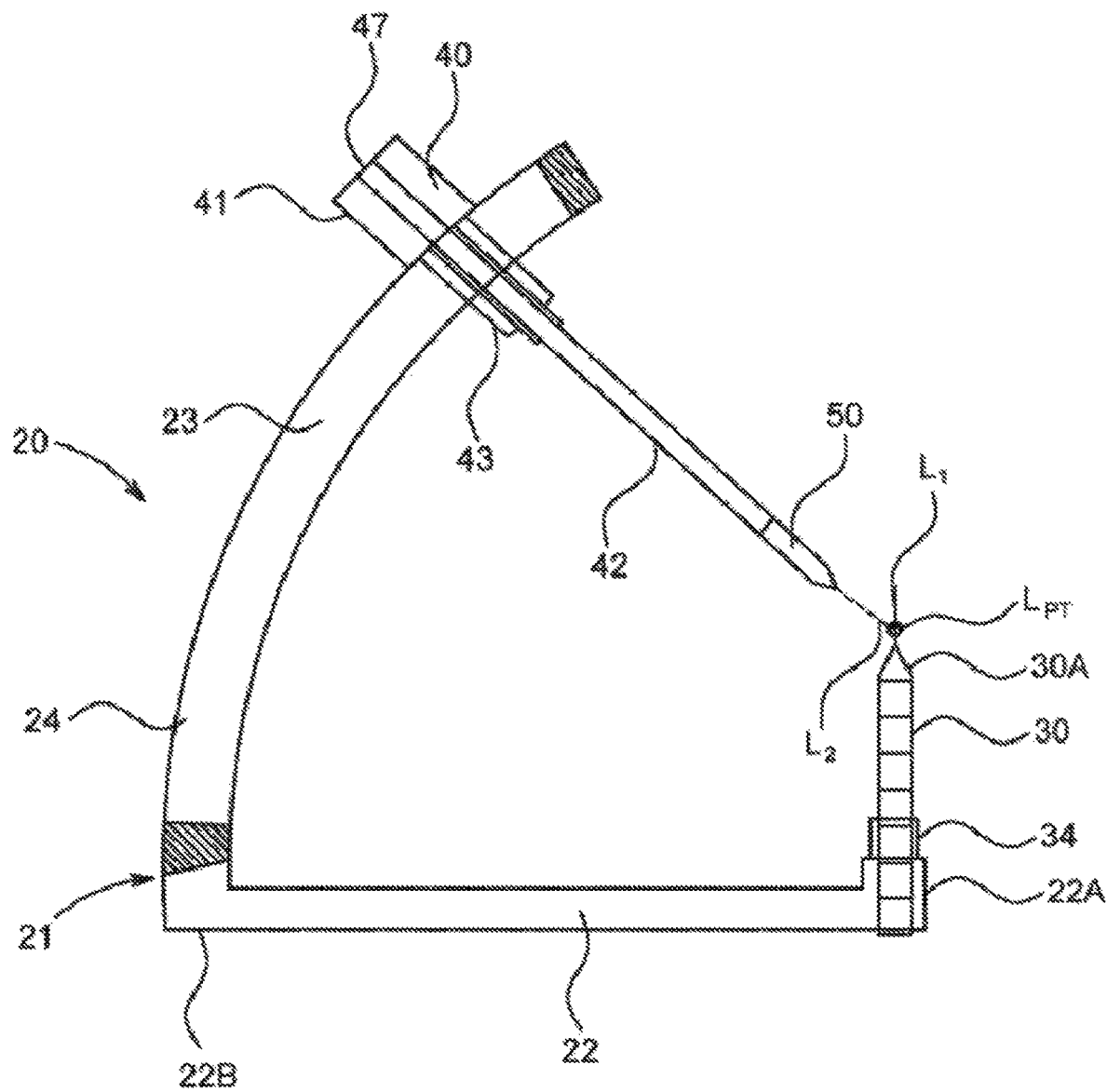
FIG. 4 demonstrates the guide system of the first embodiment of the present invention.

FIG. 4 demonstrates what the guide system 20 looks like. It demonstrates how an intra articular guide pinning member 30 is placed, how the guide component 21 then attaches to the pinning member 30 at an appropriate depth. The guide component 21 has a swinging arcuate arm 24 that comes around and allows the precise localization and alignment tip to tip even though one can't see what is essentially a blind tip 10A. This allows access for things you can't see. Again, completely eclipses any type of current prior art using poor techniques such as fluoro, etc. for visualization. With the present invention, the surgeon knows exactly where he is with precise localization for addressing the lesion in a completely different way of practicing medicine.

Figure 5:
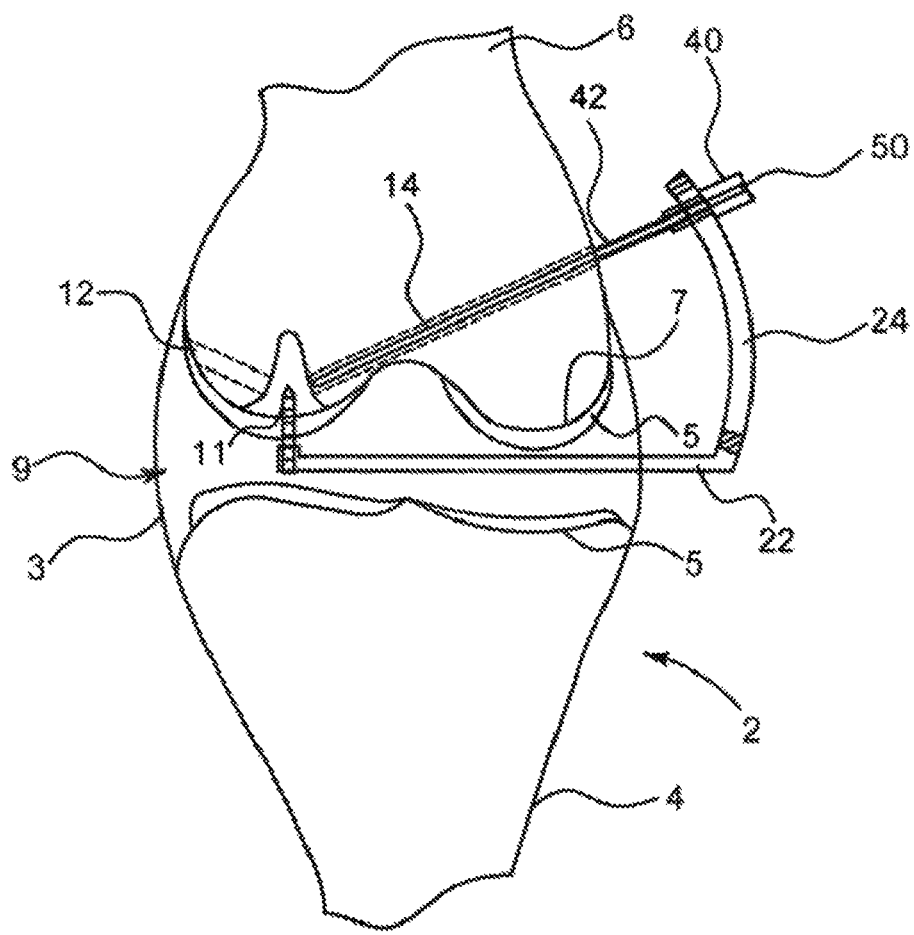
FIG. 5 is a second view of the joint of FIG. 1 showing an additional entry access with the guide system of the first embodiment in place.
Figure 6:
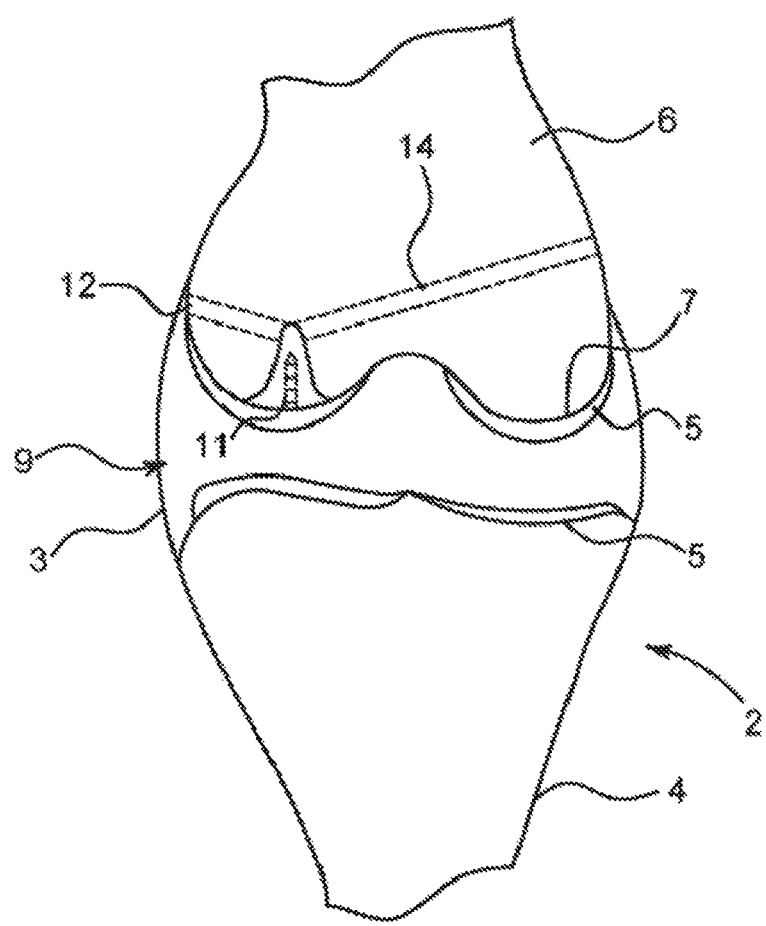
FIG. 6 shows the second view with the guide system of the first embodiment removed.
Figure 7:
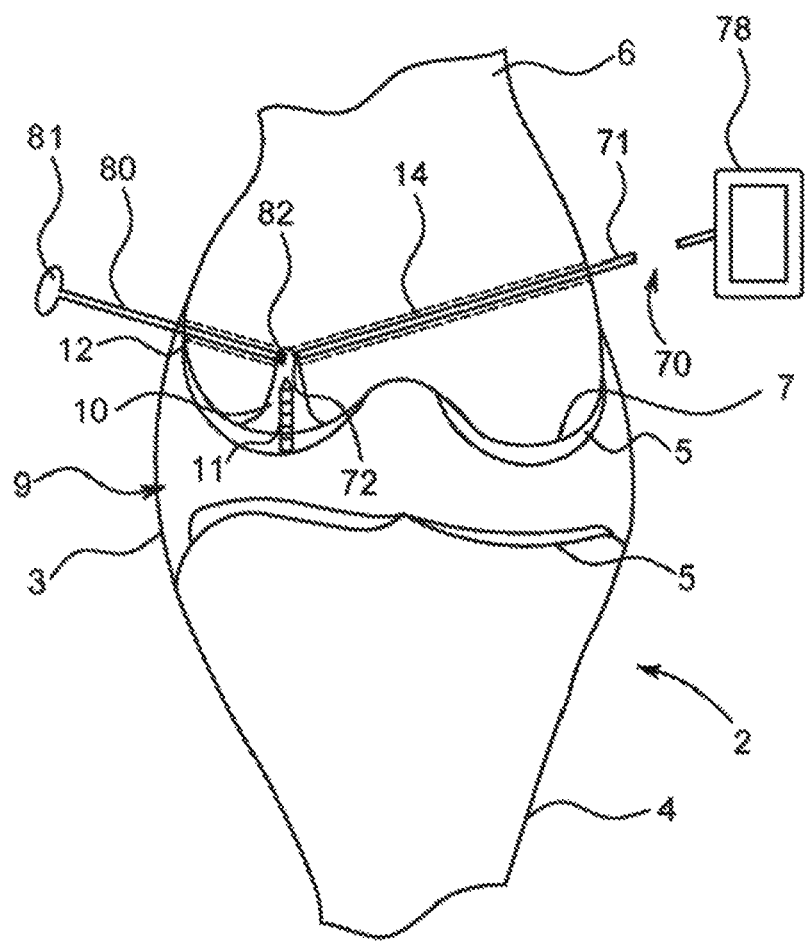
FIG. 7 shows a camera in the second entry access.

As shown in FIG. 4, the guide system 20 has a guide component 21. The guide component 21 has a straight first arm portion 22 that extends in a straight path to an end 22A for holding a pinning member 30. The end 22A is transverse to the arm portion 22. As shown, the shank of the pinning member 30 has marked gradations 33 that establish the distance to the tip or point 30A. The pinning member 30 can be a pin, a drill bit or punch, by way of example. At the end 22A, a shank tightening nut 34 or fixation device is shown that, when tightened, holds the pinning member 30 securely to the arm 22 thereby fixing the tip 30A location. At the opposite end 22B of the first or straight arm 22 is a second swing or arcuate arm 24. The second arm 24 is shown in a partial section view showing a slot 23 that allows a movable guide 40 to slide in the slot 23 over a range of angles between at least 0 and 90 degrees relative to the tip of the pinning member 30, most typically between 30 and 60 degrees. Preferably, the movable guide 40 has a cannulated shaft, sleeve or tube 42 with a tightening clamp 41 having a nut 43 that fixes the movable guide 40 onto the second arm 24 anywhere along the slotted opening or slot 23. As shown, a drill bit, a punch or a trocar 50 can be slipped through the movable guide 40 tube 42 to create the second access portal or track 12, 14. Preferably, when locating the desired location to form the second or additional access portals, the tube 42 is moved relative to the guide 21 to set the tube solidly against the tissue then the components are tightened to fix the angle and the sleeve length. Then the drill 50 can be inserted to create the second or more access tracks or portals 12, 14. The shape of the guide component 21 allows the system 20 to be pinned at one location and flipped to an opposite side of the knee joint while still pinned if desired to make additional or even third or more access portals or tracks as shown in FIG. 5. This feature makes the procedure to create additional entry points remarkably easy. Once the two access portals 12, 14 are created, the use of a visualizing camera system 70 as the surgeon uses other devices and instruments to remove or repair the lesion 10 is available so real time observation of the surgical repair is available which vastly improves the likelihood of successful lesion tissue removal and treatment. Once the lesion 10 cavity is cleared, substances 62 can be added through the access portal. One such substance 62 is bone cement that can greatly improve screw or pin fixation.

Essentially the next aspect of this is taking bone marrow lesions 10 with ocd and osteochondritis dissecans and when the surgeon is trying to fix these, generally the bone 7 behind it is poor so he is not getting very good fixation so the two additional elements are needed after one utilizes the technique, either after or during utilization of the technique the surgeon can actually put screws in place, they can be metal or they can be biocomposite. These fixation devices 90 actually go into the lesion 10 then he can put the substance 62 around it, the grout or a bone cement which may include different types of bone cement, different types of putty 62, which might harden when set actually allow the screw to be better fixed, alternatively he can put the bone cement substance 62 in the lesion cavity first, then screw directly through it which can again both of these provide better fixation than without any of the bone substances 62. The cement is either put around once the screws are placed or the screws 90 are placed through it. And these can be screws or these can be darts or any variety of fixation devices 90.

FIG. 8 is the picture showing what an OCD lesion would look like intra articular, you can see the cartilage wrap 5 coming off and the subchondral bone 7 behind it. Often you can't see the bone behind it. This one is a lesion 10 that is more advanced and fixation pins 90 are placed to stabilize the bone.

FIG. 9 is a picture with 3 photos 9A, 9B and 9C above it showing how a lesion 10 has completely come off and that is what the bone 7 looks behind it. There is more dead bone behind that we want to access so either you could have a cartilage cap that was intact on it or you have the exposed bone. That is why with the guide system 20 one can go through either cartilage 5 or intact bone 7 when it is exposed. That bone is called subchondral bone 7. Again, the surgeon wants to get behind it and he can't see it, that's why he wants to pass the tip or end of the pinning member and that's the tip end that he wants to access blindly from a different portal 12, 14. One can see on FIG. 9 that's the x-ray which shows what a lesion 10 like this might look like, and one can try to pin that lesion or try to get behind it.

The FIG. 8 illustration of this is an actual photograph just shows how one currently can secure that lesion 10, stabilize with screws or degradable pins 90, 92. The present invention technique is more predicated upon actually a couple of different things. Number one addressing the tissue behind that bone and then more importantly, once that has been actually addressed that tissue, where bone marrow lesion has been removed can be filled with substances such as cement, etc. Now the surgeon can fix into those substances which is another extension of this system because one of the things now that can be done because one has created an appropriate bed behind that lesion you now have new techniques of fixation which can actually fix into that bone which currently cannot be done because there is no way of stressing that foundation absent this type of repair.

The second or the first entry access itself or the track created can be enlarged. It's important to note that the second entry access, although generally extra-articular, does not necessarily have to be so. More importantly, this access track can be away from the cartilage and subchondral bone so that it does not damage these structures. The current state of the art does not allow for addressing lesions of bone distant to the entry point of the localizing site. It is also important to restate that the present inventive technique allows for accessing or accessing as well as addressing the lesion. Specifically, although the surgeon can address bone lesions by removing damaged tissue, sometimes he can choose to address them by simply adding structural materials or stem cells or both without removing any tissue.

An important feature of this technique is that fixation of the lesion utilizing stabilizing devices such as the initial localizing pin or additional ones which can now either be drilled or punched through the lesion and then be filled with the grout material, such as concrete being poured on rebar, or filling with the grout material before and then the fixation device is placed through it, such as placing screws through concrete once it has set. This introduces an entirely new methodology of addressing these lesions which previously has not been effectively or precisely performed.

With reference to FIGS. 10-12, a normal joint with a lesion 10 is shown where the lesion has been prepared forming a cavity in the region 10 and 10A. In this cavity, bone anchors, screws, or anchors or pins 90 can be positioned as illustrated in FIG. 10. These pins and screws 90 enter into the cavity location as shown in FIG. 10. With reference to FIG. 11, when a syringe 60 is positioned into the entry access 12, the syringe filled with bone cement 62 can be used to deliver bone cement or other adhesive or bonding material into the cavity 10 or 10A of the lesion 10. When this occurs, the bone cement 62 encapsulates and surrounds the anchors 90 that have previously been positioned as illustrated in FIG. 10. As the cement fills the cavity, the syringe 60 can be backed out and as illustrated in FIG. 10, the entire entry access portal 12 can be filled. This provides a secure structurally enhanced repair of the area where the lesion 10 or abnormality had existed, as illustrated in FIG. 12. Alternatively, a bone repair mixture 62 can be inserted into the cavity via the entry access portal 12 and then the screws or pins 90 can be positioned drilling into the cement 62. If the cement 62 is soft, it will simply go into the cavity and will surround the screws or pins 90 with the cement 62 which will harden later or alternatively if provided with sufficient cutting flutes, can be threaded into the prepared area with the cement 62 already hardened. Any of these methodologies are possible with the benefit that the damaged knee will be strengthened substantially by the introduction of the bone hardening cement 62 into the cavity 10, 10A via the entry access 12.

Figure 14:
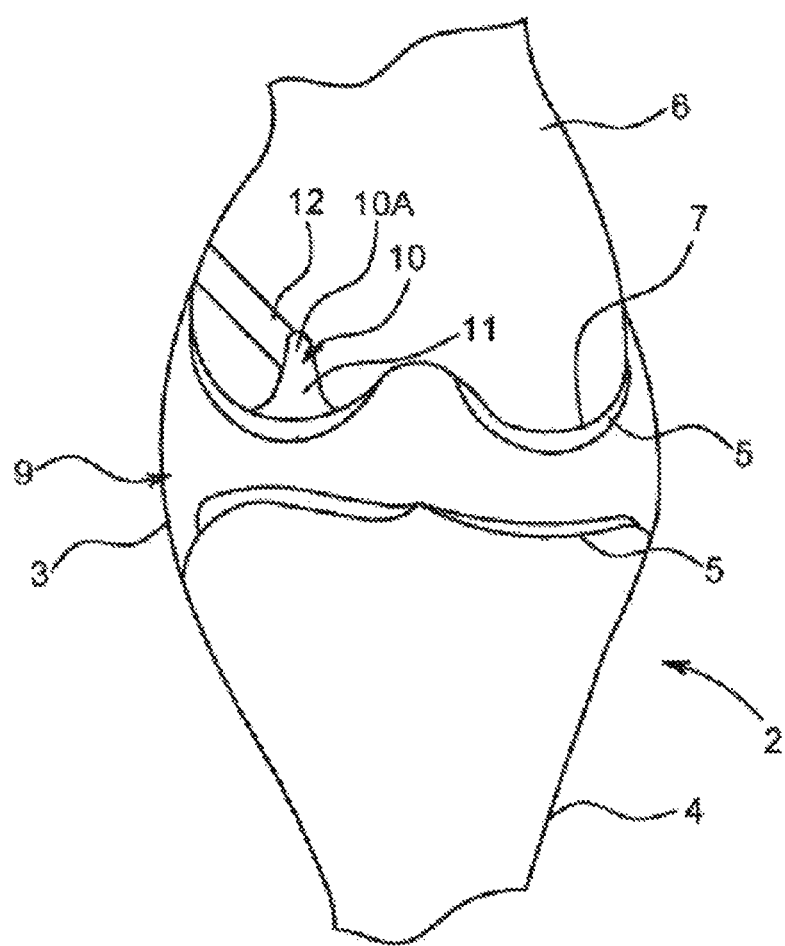
FIG. 14 shows the created second entry access to the lesion without a physical access through the subchondral bone or cartilage when performing the method of the second embodiment.
Figure 15:
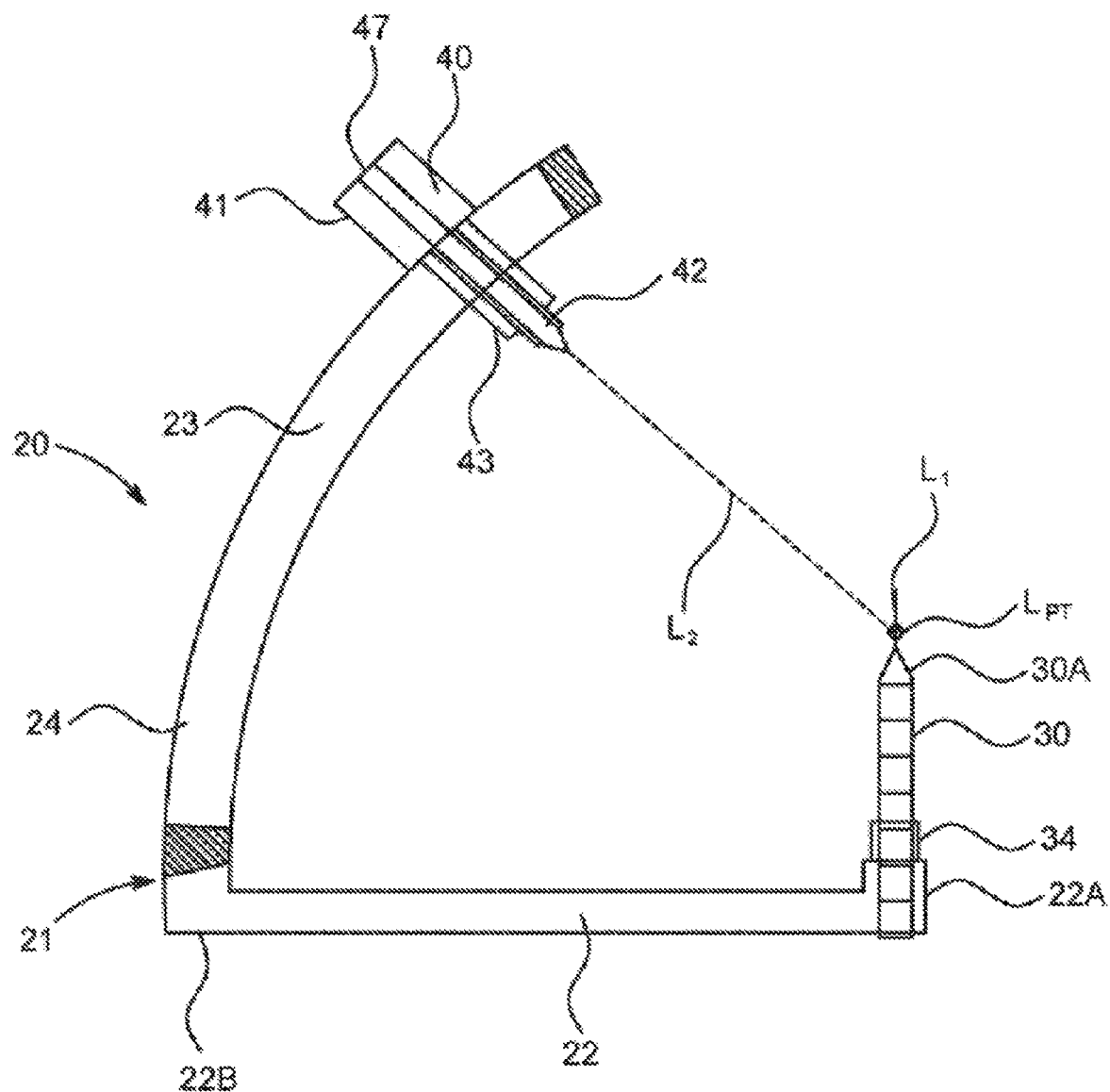
FIG. 15 is a plan view of the guide system of the second embodiment.
Figure 16:
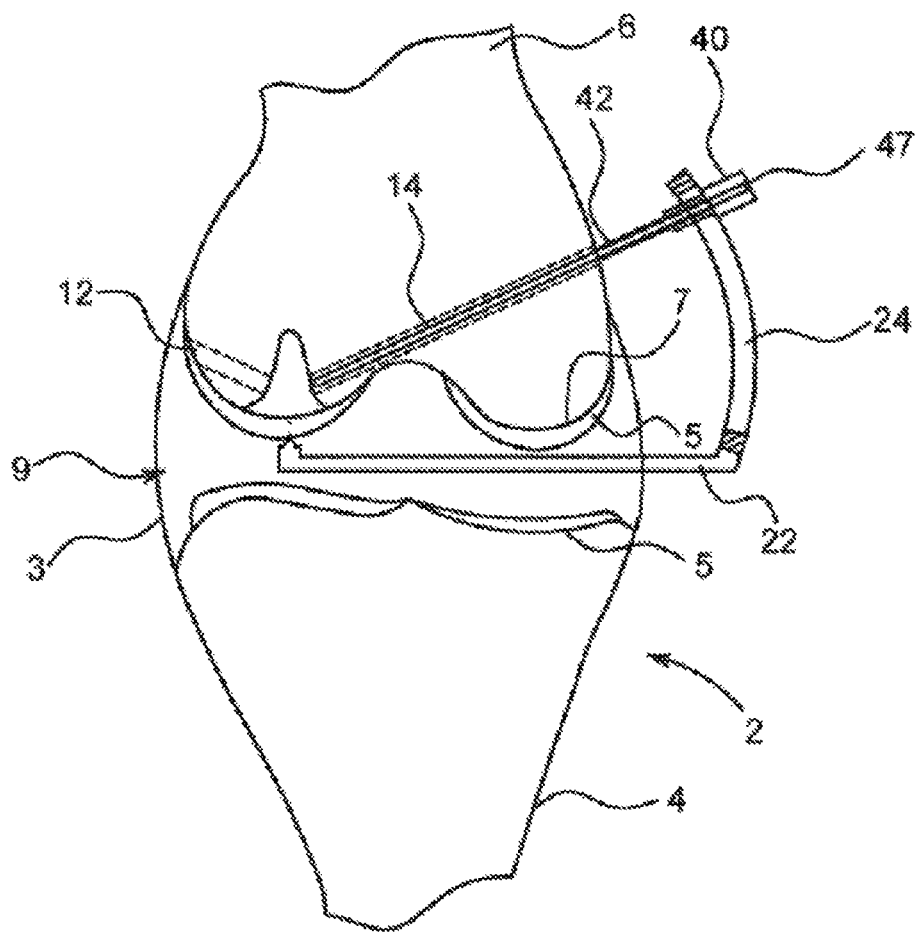
FIG. 16 is a second view of the joint of FIG. 15 showing an additional entry access with the guide system of the second embodiment in place.
Figure 17:
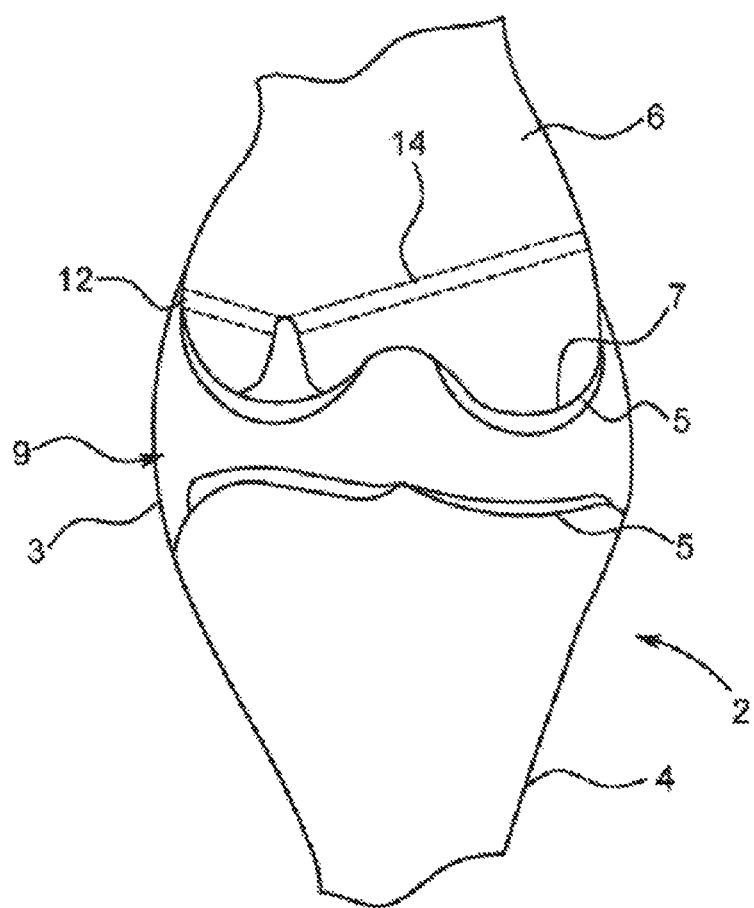
FIG. 17 shows the second view with the guide system of the second embodiment removed.
Figure 18:
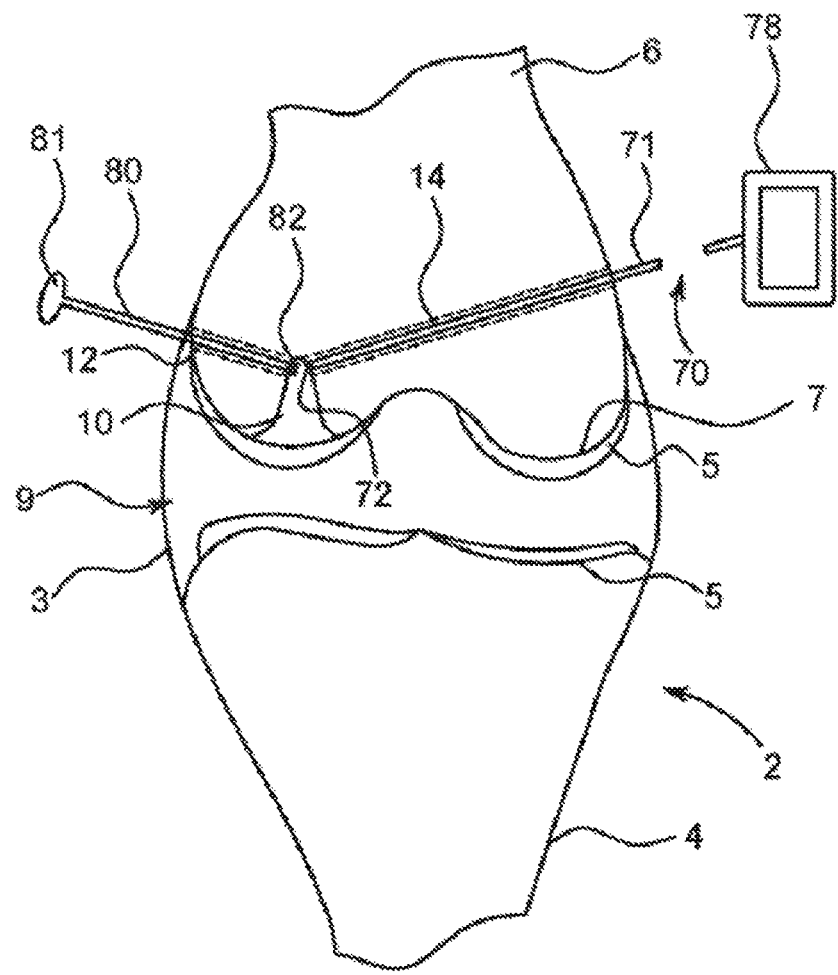
FIG. 18 shows a camera in the second entry access.

With reference to FIGS. 13-18, a second embodiment of the invention is shown. The second embodiment uses a guide component 21 similar to the guide component 21 of the first embodiment. However, in this embodiment, the localizing pinning member 30 is short, shown truncated, having a point or tip 30A that can rest onto the cartilage 5 above the subchondral bone 7. In this location 11A, the tip 30A can be pinned onto the cartilage 5 so that it is held there by the surgeon and the entry access portal 12 can be created using the movable guide 40. The movable guide 40 can then have a drill, punch or trocar 50 directed into the bone towards the lesion 10 to create an entry access portal 12. As illustrated in FIG. 14, the entry access portal 12 is shown approaching the region of the lesion 10 and is delivered to a desired target location within the lesion. What is unique about the second embodiment method is, as shown in FIG. 14, there is no hole or first entry access tunnel 11 created by the localizing pinning member 30 instead a virtual pathway 11V is created by the guide component 21. As shown in FIG. 15, the guide component 21 has the arcuate arm 24 with the movable guide 40 that can be positioned anywhere along the angular approach of the arcuate arm portion 24. The straight arm portion 22 holds the localized pinning member 30. The localized pinning member 30 may have gradations 33 as previously discussed along the shank of the pinning member 30. However, the pinning member 30 has an end 30A that rests on top of the cartilage 5 and subchondral bone 7 such that a virtual pathway 11V along line $L_1$ is created pointing into the lesion 10. If desired, when the movable guide 40 is positioned along the arcuate arm portion 24, a second line $L_2$ is created. The intersection of lines $L_1$ and $L_2$ creates the desired target location or point $L_{PT}$ as illustrated. The benefit of this component is that no cartilage or subchondral bone needs to be cut or drilled into using this device. As shown in FIG. 16, the entry access portal 14 is already created using the virtual pathway 11V that was further described with reference to FIG. 13. In FIG. 16, however, the device can be then pivoted in such a fashion that an additional access portal 14 can be created on an opposite side of the joint as illustrated. Again, when pivoting the guide 21, the subchondral bone and cartilage are never penetrated through, however, all access portals will be directed along the virtual pathway 11V of the localized pinning member 30. With reference to FIG. 17, multiple entry access portals 12 and 14 are illustrated. With reference to FIG. 18, a device 80, 81 is shown on one side with the device 70 with a camera viewing the area of the lesion 10 through the additional access portal 14. In this fashion, the device 80 can be used to probe into the cavity where the surgeon observes what is happening using the camera 70.

Figure 19:
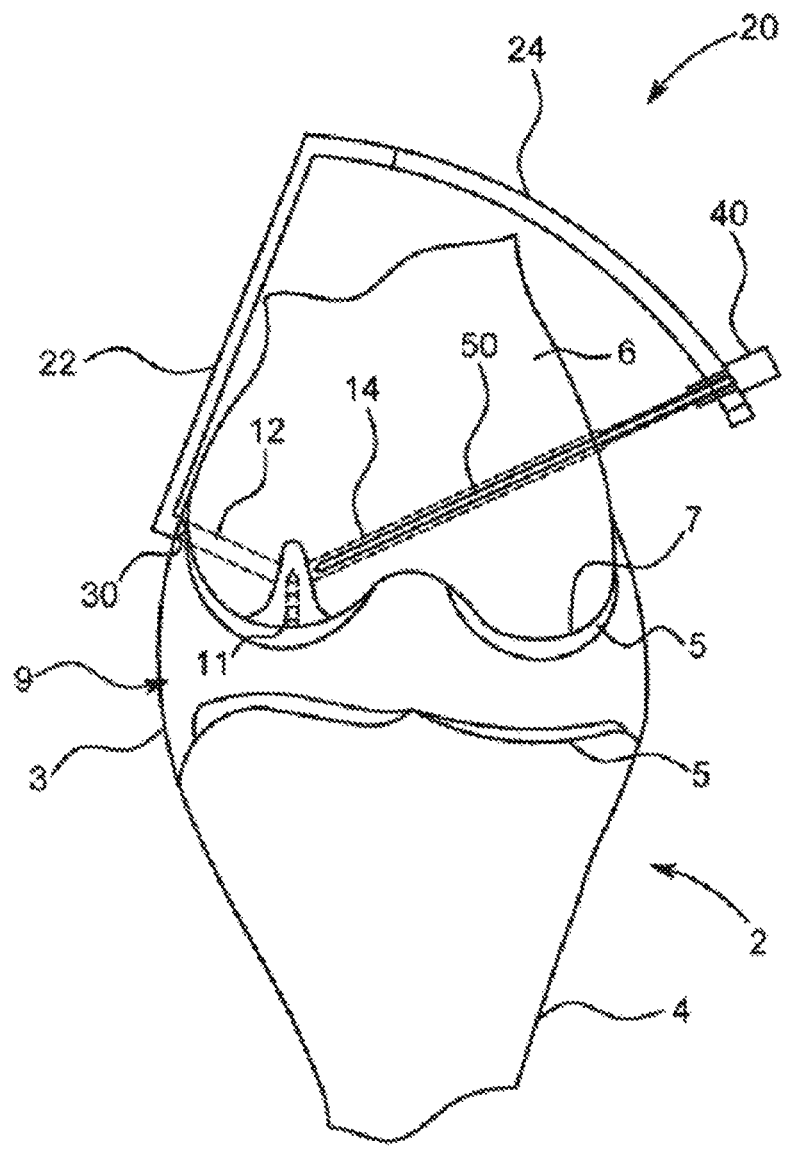
FIG. 19 is a use of either guide component wherein the localizing pining member is moved to the second access entry to create additional access entry.

With reference to FIG. 19, the guide component 21 can be repositioned such that the localized pinning member 30 is positioned in the entry access 12. When this occurs, the surgeon can locate an additional location for an entry access or an additional entry access 14 by simply pivoting the guide component 21 about the localized pinning member 30 positioned in the access portal 12 in such a fashion that the movable guide 40 can then be positioned and directed such that an additional entry access portal 14 can be drilled on the opposite side of the bone. In the embodiment of FIG. 19, a pin 90 is shown positioned in the area of the lesion 10. This method of moving the localized pinning member 30 to an entry access portal for making additional entry access portals can be used with either the first embodiment of the invention or the second embodiment of the invention.

Figure 20:
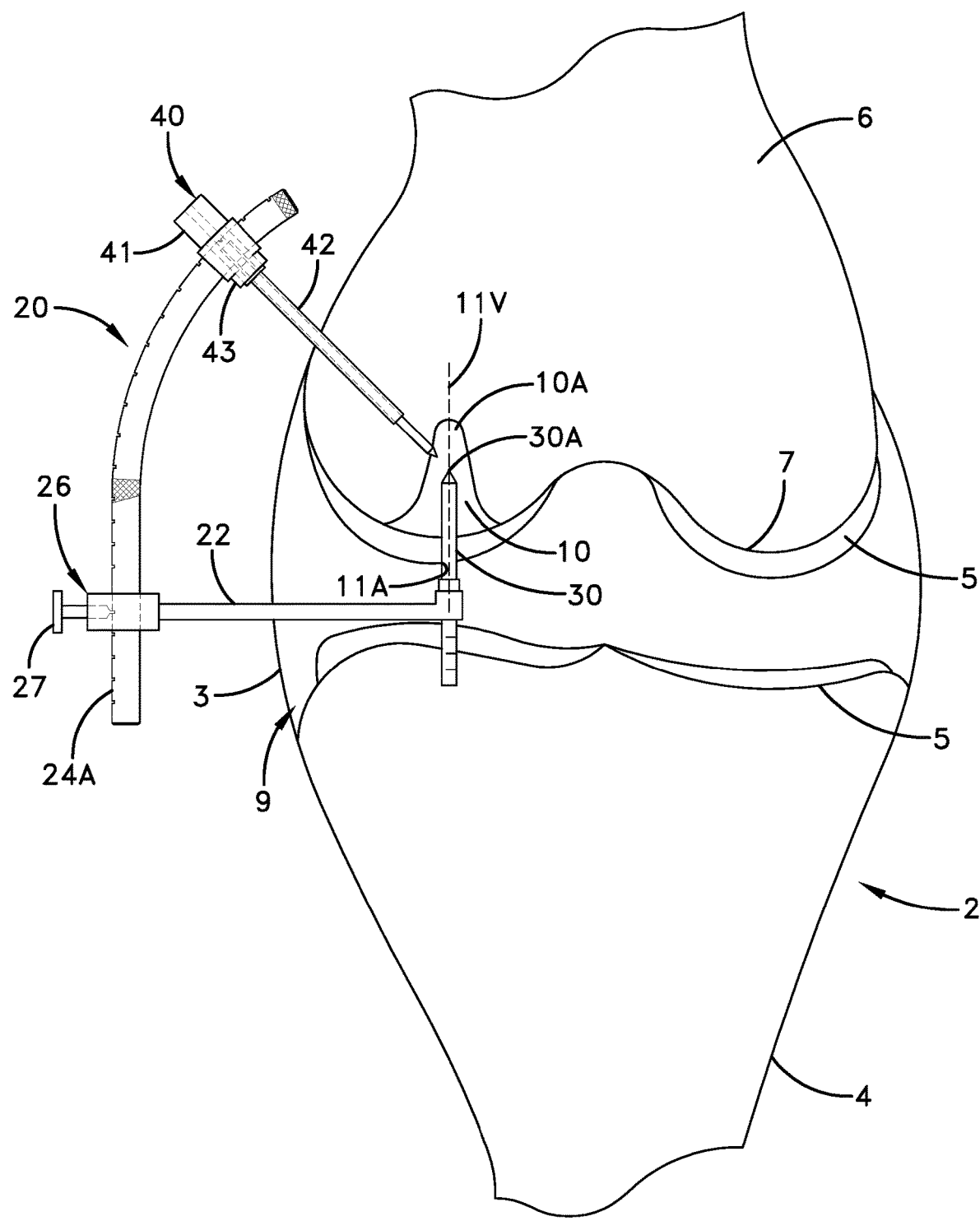
FIG. 20 demonstrates the guide system of the third embodiment of the invention wherein the guide component second arm is adjustably movable relative to the first arm, as shown the first arm has a virtual localizing pin of the second embodiment.
Figure 20A:
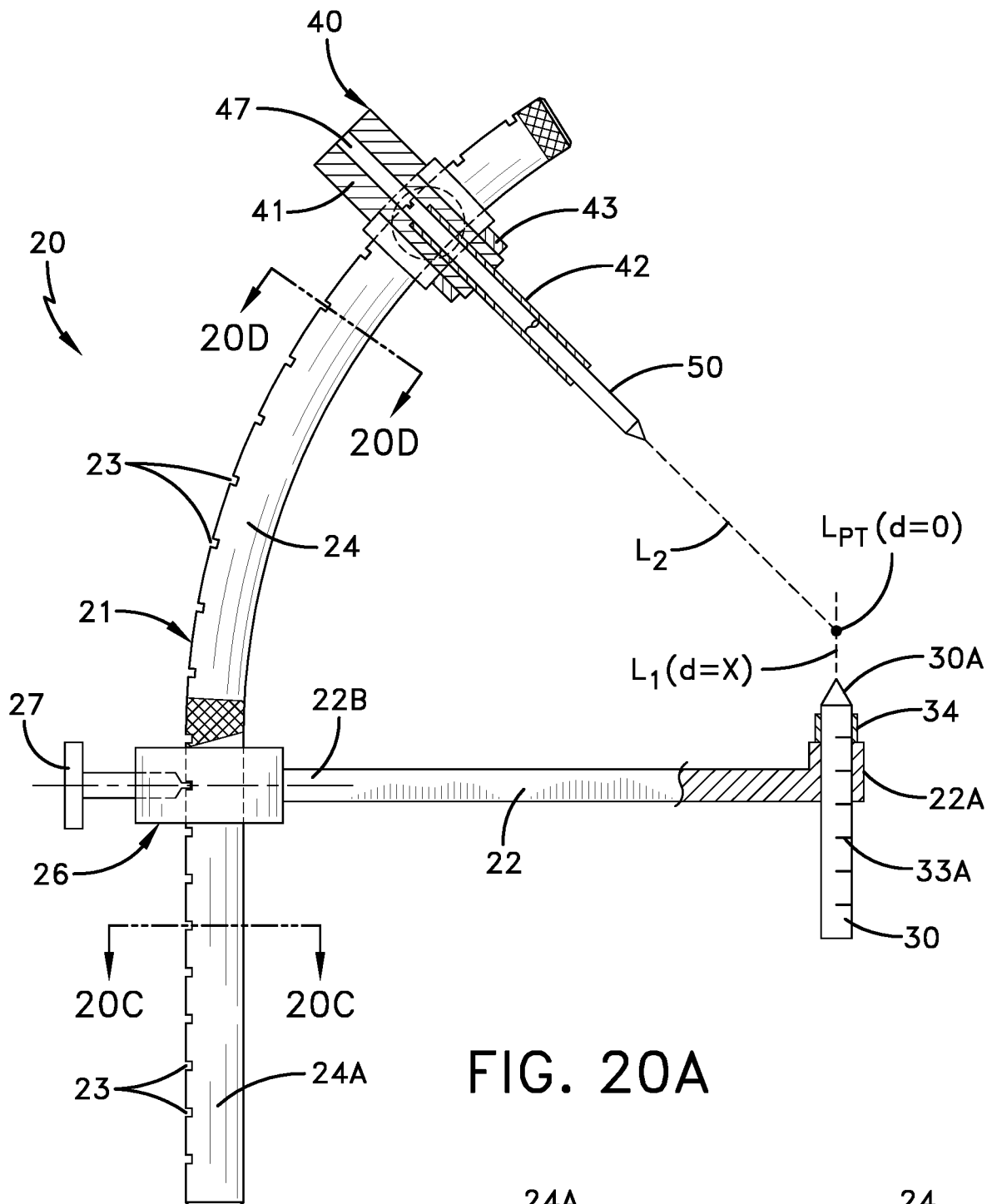
FIG. 20A demonstrates an alternative version of the third embodiment wherein the first arm has an adjustable localizing pion member of the first embodiment.
Figure 20C:
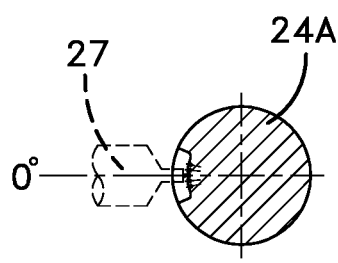
FIG. 20C is a cross-sectional view of the straight portion of the guide component taken along lines 20C-20C of FIG. 20A.
Figure 20D:
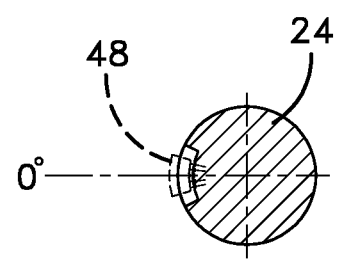
FIG. 20D is a cross-sectional view of the arcuate portion of the guide component taken along lines 20D-20D.
Figure 20B:
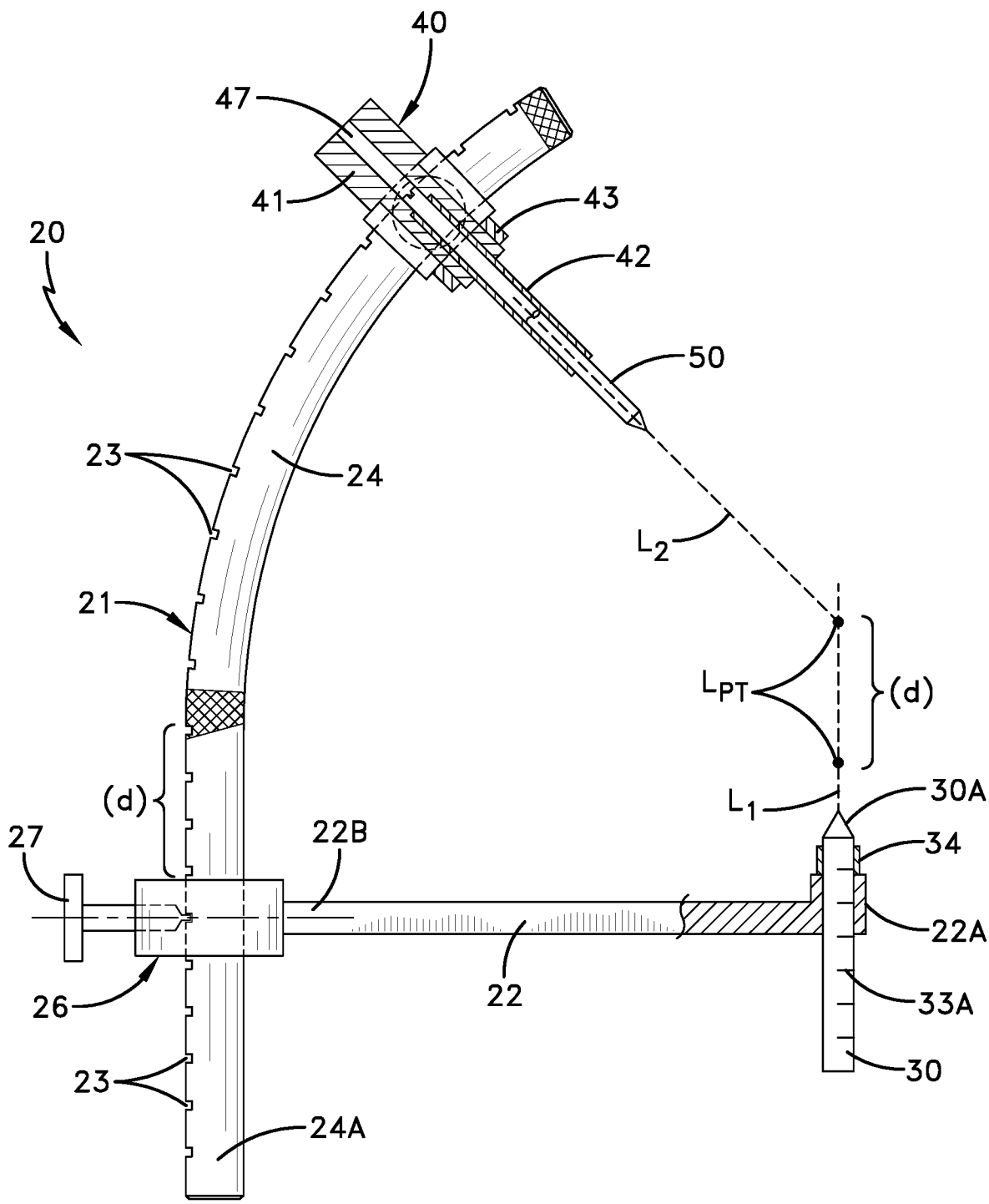
FIG. 20B shows the guide system of the third embodiment wherein the second arm is shown moved a selected distance (d) relative to the first arm wherein this adjustment moves the intersect location Lpt by the selected distance (d) thereby shift the first entry access parallel to the initial setting per-translated to allow a redirected shifted Lpt intersect.
Figure 21:
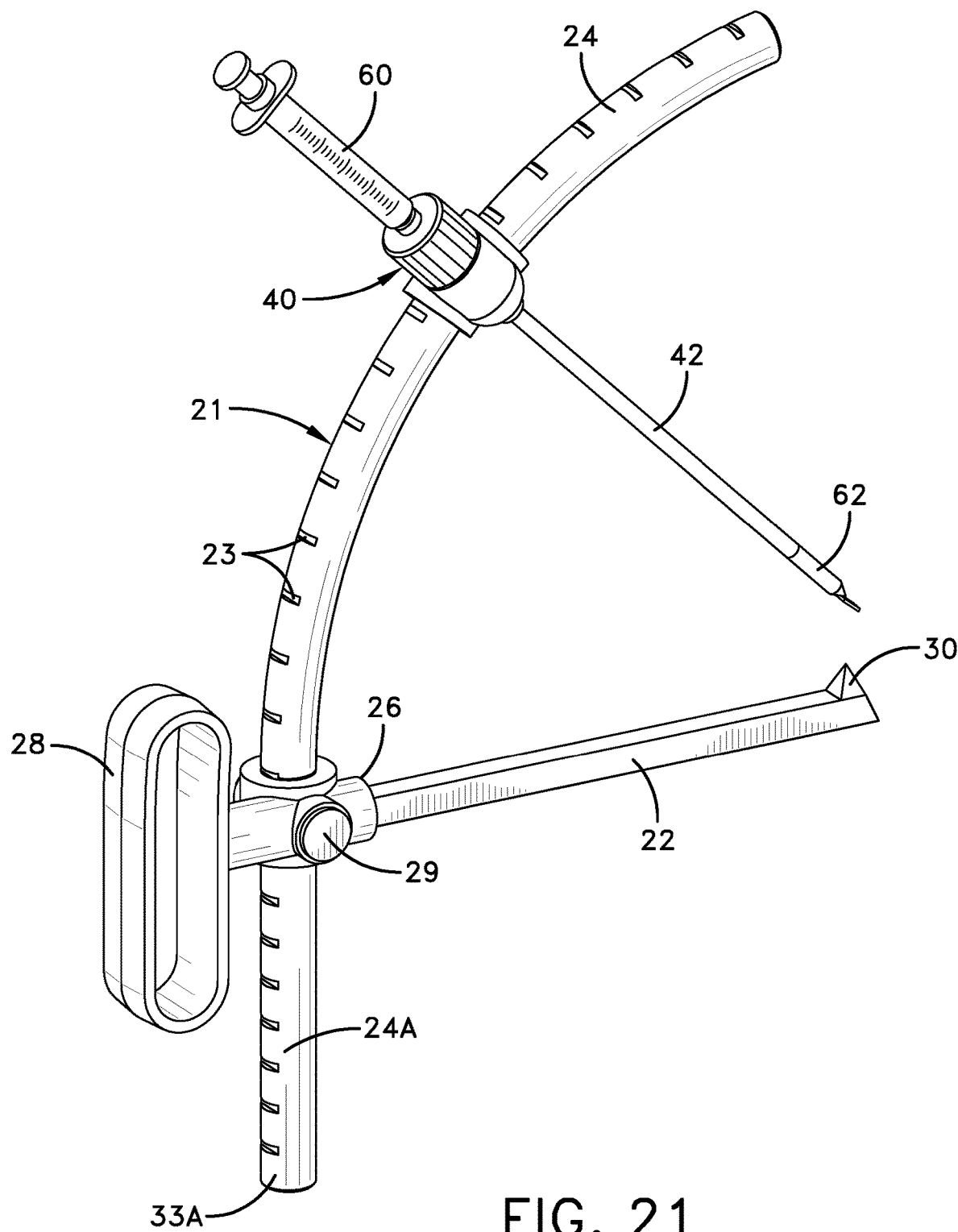
FIG. 21 is a perspective view of the third embodiment with an alternative guide component showing a syringe positioned to fill a prepared lesion.
Figure 22:
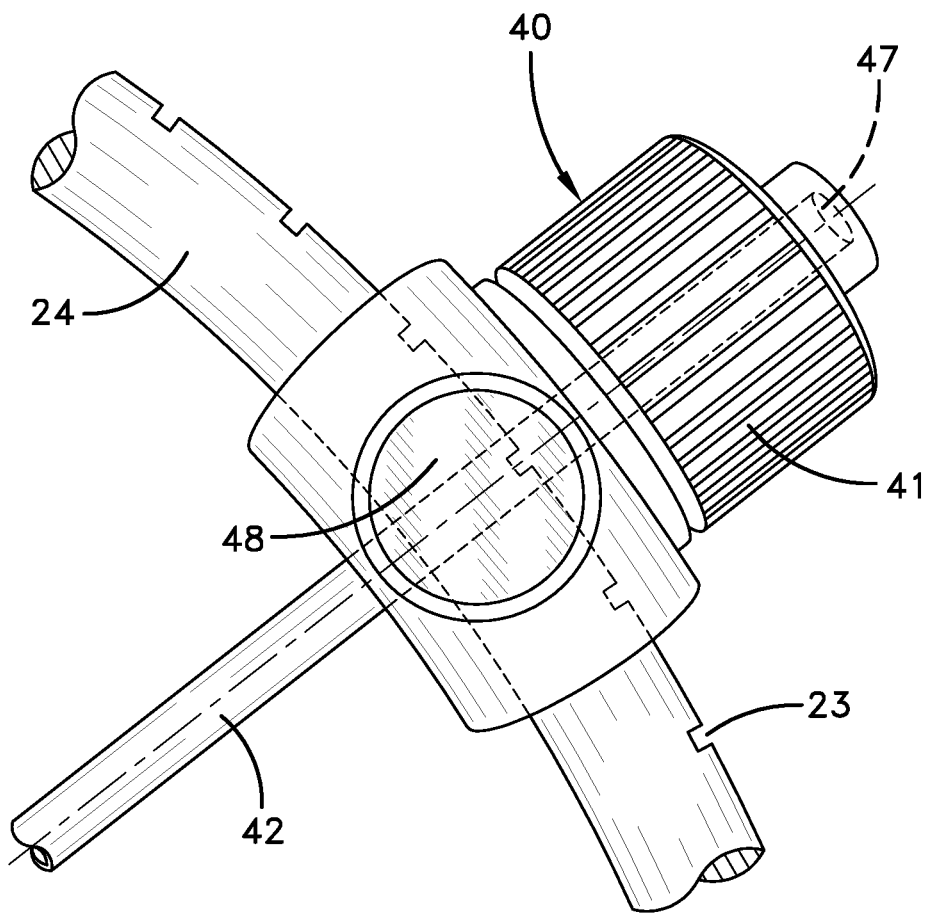
FIG. 22 is an enlarged view of the movable guide of the third embodiment.
Figure 23:
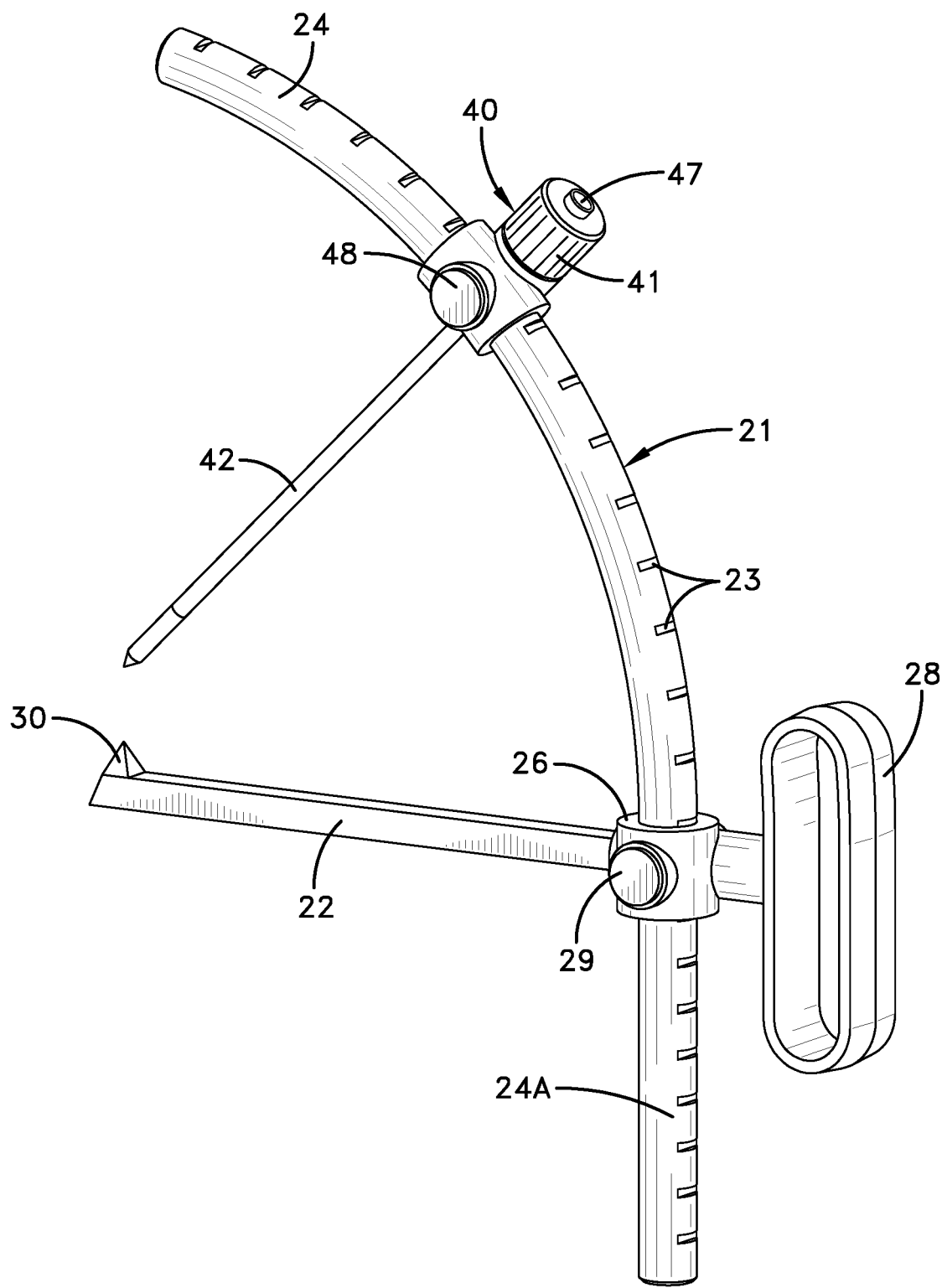
FIG. 23 is a second perspective view taken from FIG. 21 without the syringe.
Figure 26:
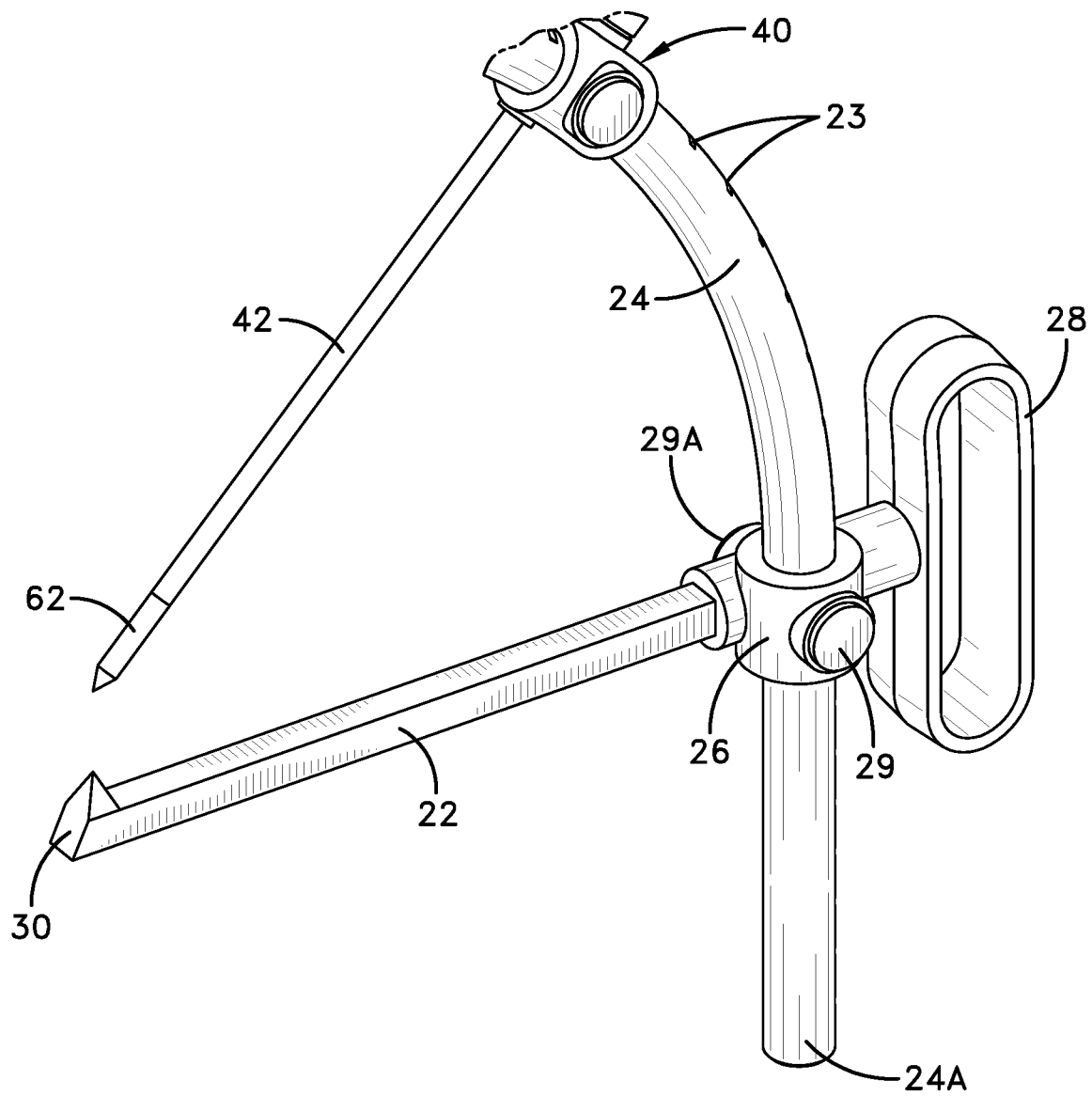
FIG. 26 shows a portion of the third embodiment guide system and the drill extending through the guide sleeve.

With reference to FIGS. 20-27, the present invention is shown with a third embodiment having a guide component that is suitable for use with the virtual pathway concept of the second embodiment as shown in FIG. 20, 21, 26 or the localizing pinning member 30 of the first embodiment as illustrated in FIGS. 20A and 20B. The guide component 21 has the first arm 22 for holding the localizing pinning member 30 detachable from the device. The first arm 22 is coupled to a coupling end 26. The coupling end 26 is configured to move along a straight portion 24A of the second arm 24. The straight portion 24A extends to the curved arcuate portion of the second arm 24. As illustrated in FIGS. 20, 20A and 20B the second arm 24 is shown having a plurality of spaced notches 23 that allows the movable guide 40 to slide into the notches 23 over a range of discreet angles spaced in increments of 3 degrees or more, typically about 5 degrees about the arcuate portion. As in previous embodiments, the second arm 24 is shown in a partial section view showing notches 23 that allows a movable guide 40 to slide in one of the notches 23 over a range of angles between at least 0 and 90 degrees relative to the tip of the pinning member 30, most typically between 30 and 60 degrees. Preferably, the movable guide 40 has a cannulated shaft, sleeve or tube 42 with a tightening clamp 41 having a nut 43 that fixes the movable guide 40 onto the second arm 24 anywhere along the plurality of notches 23. As shown, a drill bit, a punch or a trocar 50 can be slipped through the movable guide 40 tube 42 to create the second access portal or track 12, 14. Preferably, when locating the desired location to form the second or additional access portals, the tube 42 is moved relative to the guide 21 to set the tube solidly against the tissue then the components are tightened to fix the angle and the sleeve length. Then the drill 50 can be inserted to create the second or more access tracks or portals 12, 14. The shape of the guide component 21 allows the system 20 to be pinned at one location and flipped to an opposite side of the knee joint while still pinned if desired to make additional or even third or more access portals or tracks as shown in FIG. 5. This feature makes the procedure to create additional entry points remarkably easy. Once the two access portals 12, 14 are created, the use of a visualizing camera system 70 as the surgeon uses other devices and instruments to remove or repair the lesion 10 is available so real time observation of the surgical repair is available which vastly improves the likelihood of successful lesion tissue removal and treatment. Once the lesion 10 cavity is cleared, substances 62 can be added through the access portal. One such substance 62 is bone cement that can greatly improve screw or pin fixation.

Figure 24:
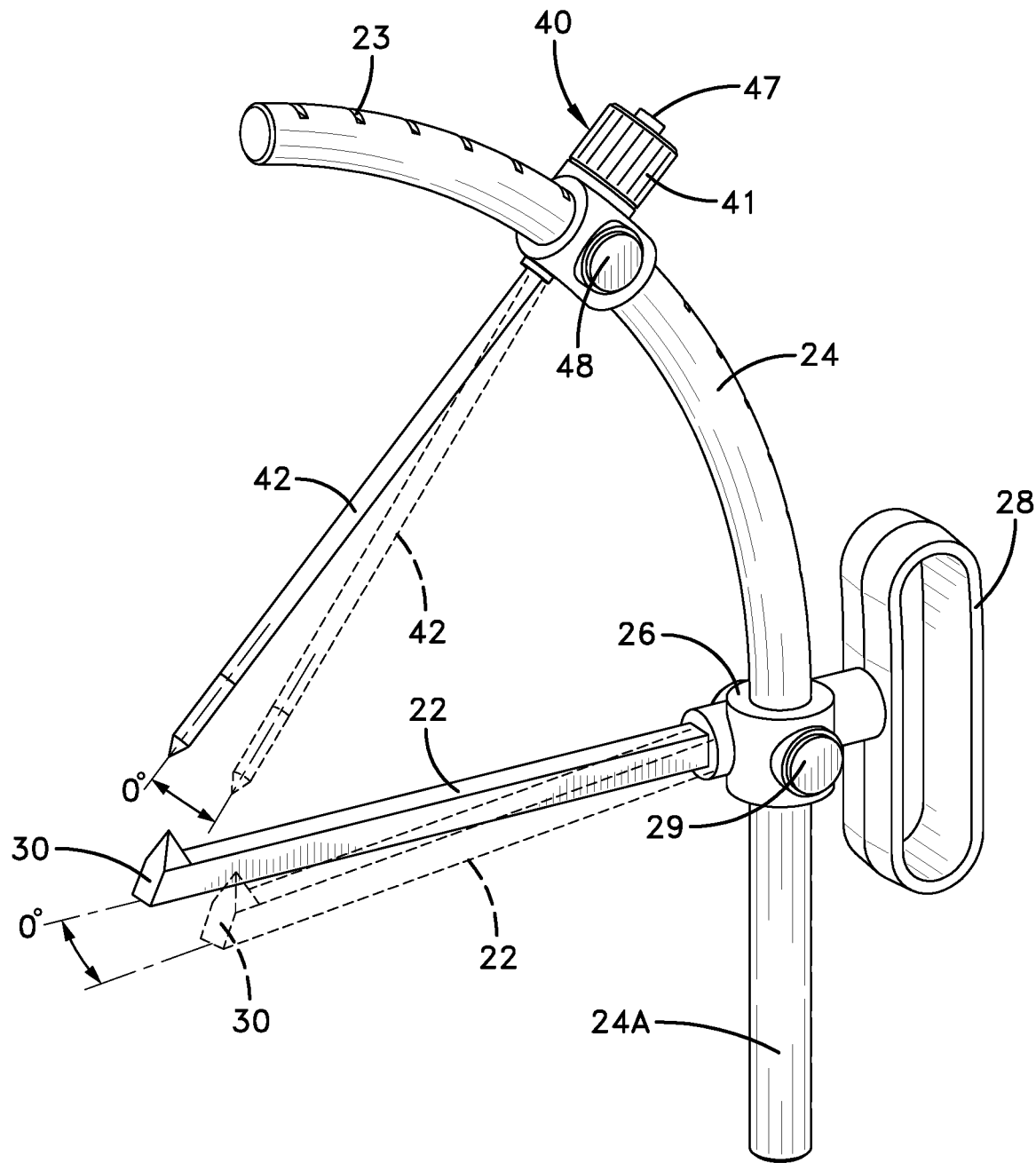
FIG. 24 is another perspective view of the third embodiment.
Figure 25:
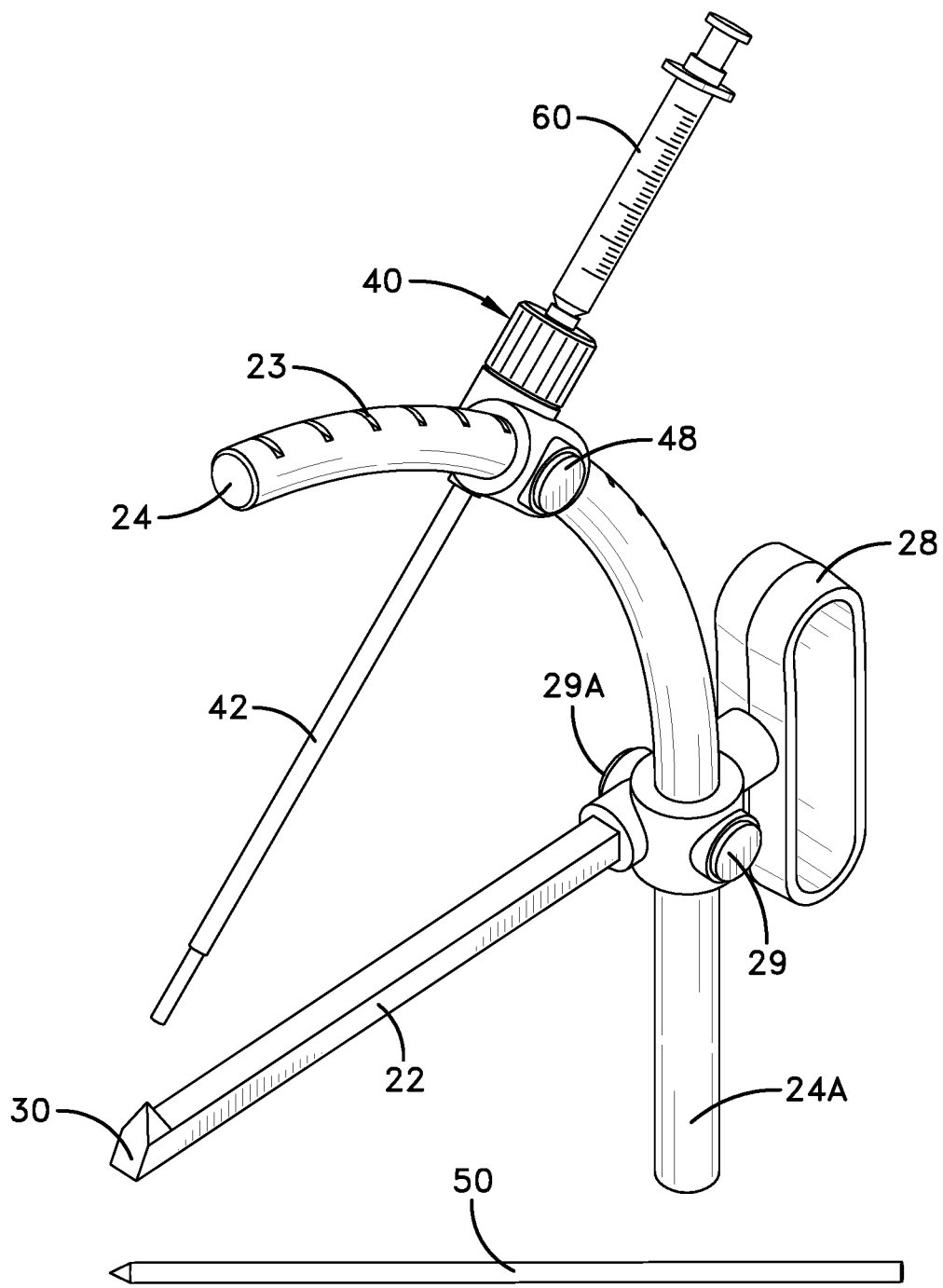
FIG. 25 shows a syringe for passing material through a cannulated sleeve in the entry access, a drill is shown in the fore view.

As shown in FIGS. 20C and 20D and best shown in FIG. 24, each notch 23 in a straight portion 24 of the guide 21 or in the arcuate portion 20 has a length extending a circumferential distance that allows the first arm with the pinning member 30 to angularly move or shift $\theta_1$ fore or aft relative to a null or 0 degree position centerline. Similarly, the movable guide 40 can be angularly moved a distance $\theta_2$. These adjustments allow the surgeon additional adjustment features for different anatomical features. This adjustment from the centerline causes the virtual pathway or the selected path to shift so as not to intersect by an adjustment amount selected by the physician providing additional flexibility during a procedure.

What is clearly different from the first two embodiments is the straight portion 24A provides a way for the surgeon to precisely adjust the track of the drill forming an entry access 14 without changing the angle established by the movable guide component 40. This is achieved by moving the second arm 24 relative to the first arm 22 from an initial position from d=0 to a shifted position by a second distance d=x by moving the coupling end 26 of the first arm 22 along the straight portion 24A by precisely having the second arm 24 moved relative to the coupling 26 and of the first arm 22. This shift by a preselected distance (x) correspondingly shifts the track of the entry access exactly a distance (x). This means the surgeon can move the entry track without altering the angle. The secondary adjustment enables the surgeon to select an optimal access to the region in or near the lesion or abnormality that is being treated. It is not uncommon for the optimal entry approach angle to provide a track that is not exactly ideal for a treatment. This added feature of adjusting an entry track by a precise offset distance allows the angulation to remain optimally fixed as the location is shifted by a pre-selected offset distance (d). This results in the initial entry access track is shifted to an offset track that is parallel to the original initial access track as the shift adjustment being clearly shown in FIGS. 20A and 20B. In FIG. 20A, the initial track $L_2$, shown in dashed lines, intersects line L at $L_{PT}$ and when the second arm 24 is shifted a distance (d) relative to the coupling 26 and locked in by a thumb screw 27 at a notch 23 spaced periodically at a distance of 1 cm to each adjacent notch 23 or any other convenient distance. The access track line $L_2$ is shifted to $L_{PT}'$ the same distance (d). This capability to adjust angulation at the arcuate portion 24 and also shift to an offset distance at the straight portion 24A affords the surgeon a convenient and very reliable way to create blind access openings for treating lesions and other abnormalities. This includes the treatment of tumors and infections in addition to the other problems discussed. Specifically, with respect to tumors, the surgeon can introduce stabilizing materials such as different types of bone substitutes as well as cement. It also allows him to deliver targeted ablation agents and chemotherapy. With respect to bone infections, it can also allow for delivery of bone agents and cement as well as antibiotics. These are both incredible indications that heretofore were never really accessible so precisely being nearly impossible to target indications.

A variation of the system for accessing extra articular lesions or abnormalities of the third embodiment is illustrated in FIGS. 21-26. In this variation, the guide component 21 is made in a simplified structure where the second arm 24 is made as a solid rod having a straight portion 24A and an arcuate portion 24 formed as a single piece with the notches 23. As shown, the movable coupling 26 and the movable guide 40 are simply slipped onto the guide component 21. The notches 23 that act as calibration indentations, similar to the calibrations 33A of the localizing pin 30, are shown extending all along the guide component 21 in both the straight portion 24A and the arcuate portion 24. The movable guide 40 has a sleeve 42 detachably connected and the guide 40 has a locking button 48 which, when depressed, allows movement of the guide 40 about the arcuate arm 24 and, when released, holds the guide 40 in a fixed position preferably within a notch 23. The locking feature 48 can be constructed in a variety of alternatives such as a thumb screw or its equivalent. Similarly, the coupling 26 has a similar locking button 29 that when depressed releases so the second arm 24 along the straight portion 24A can be adjusted as previously discussed and similarly held in one of the notches 23. As shown, the device of this embodiment has a handle 28 to provide the surgeon a convenient way to hold the system 20 as he sets his access track and his offset to precisely pinpoint the track of an entry access. As noted, the device can be moved to create multiple entry access openings if so desired. At the end of the movable guide 40 is an access portal 47 provided to receive a syringe 60 or camera 72 or any other tool that may be needed to pass into an entry access opening formed by a drill 50 or punch or tap, shown in FIG. 25.

As shown in FIG. 26, the drill 50 or punch or tap is guided through the sleeve 42 when set to create an access opening. One important aspect of the system is an axis of the localized pinning member 30 and an axis of the guide sleeve 42 in every embodiment shown lie in a single plane. This insures the virtual pathway $L_1$ and the access track $L_2$ when extended will intersect. The surgeon, when creating the entry access opening, can select the depth of the opening to be created short of the point of intersection, at the point of intersection or past and beyond it. This can be done by simply drilling to a predetermined distance, the surgeon can mark on the drill 50 and when that mark is reached, he can know exactly where an end of the access opening is, which in this invention can be called the desired target location.

Figure 27:
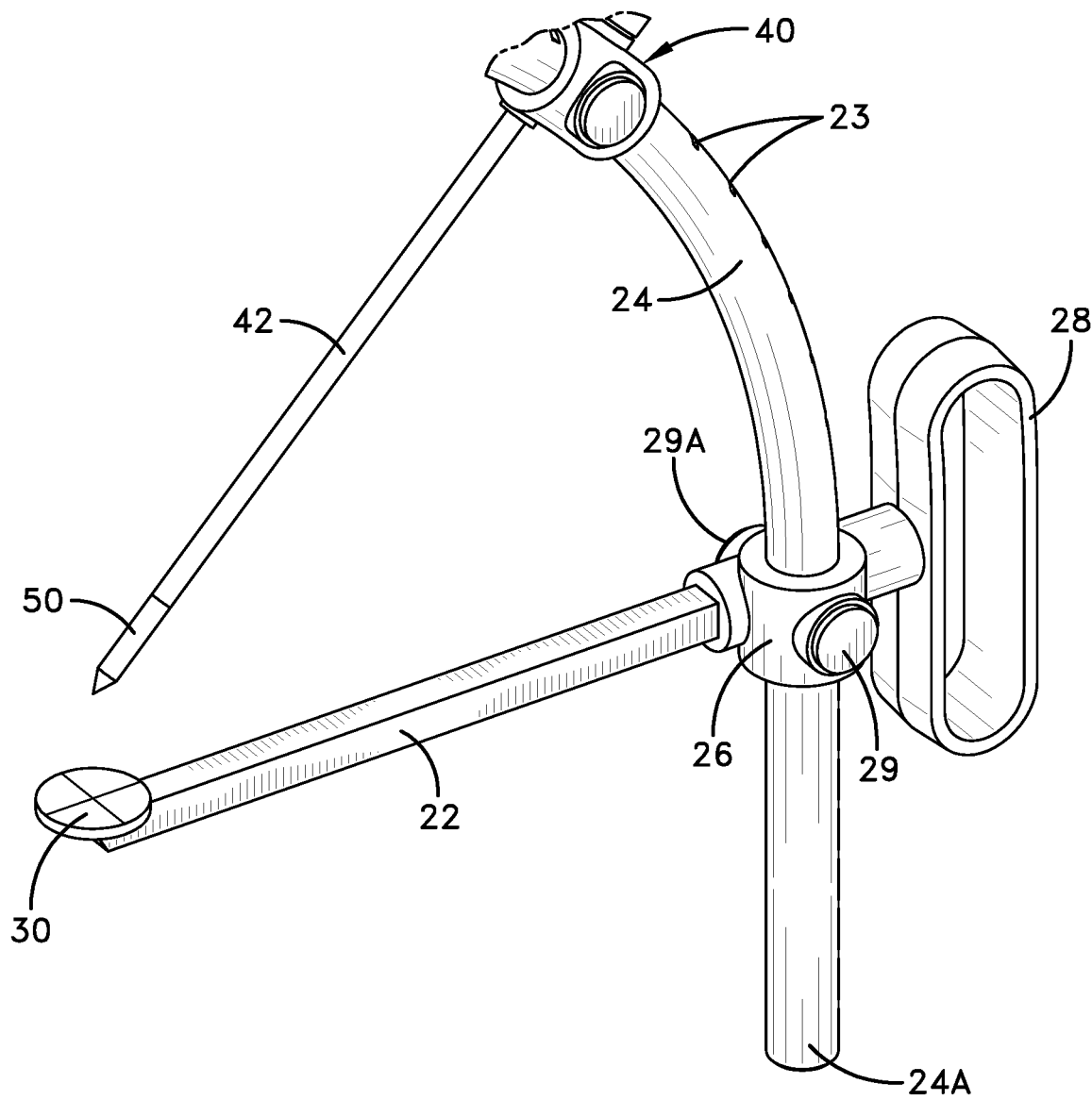
FIG. 27 shows a virtual localizing pin configured as a flat oval tip with a centered target cross-hair feature.

The system 20 shows the localizing pinning member 30 as a pointed elongated pin 30, or a short virtual pin 30. As shown in FIG. 27, the pin 30 can be made as an oval or annular ring at the end of the first arm 22. The annular ring preferably has a cross-hair centered in the opening creating a virtual target observable by the surgeon. Alternatively, the pinning member 30 can be cannulated to form an access entry sleeve if so desired.

One of the features of the present invention is it allows for intra articular, as well as extra articular, referencing of a target location or point within a bone structure anywhere in the body, not limited to a joint. Wherein the reference point allows for the access or entry to precisely occur anywhere in the bone structure, not necessarily limited to the exact location of the reference point.

With reference to FIGS. 28-32, a fourth embodiment of the guide system 20 is illustrated. This fourth embodiment has a guide component 21 with the curved or arcuate portion 24 defining the second arm and a straight portion 24A. In this embodiment, compared to the third embodiment, the notches of the third embodiment are replaced with openings 23 in the curved portion and slots or openings 25 in the straight portion 24A.

Figure 29:
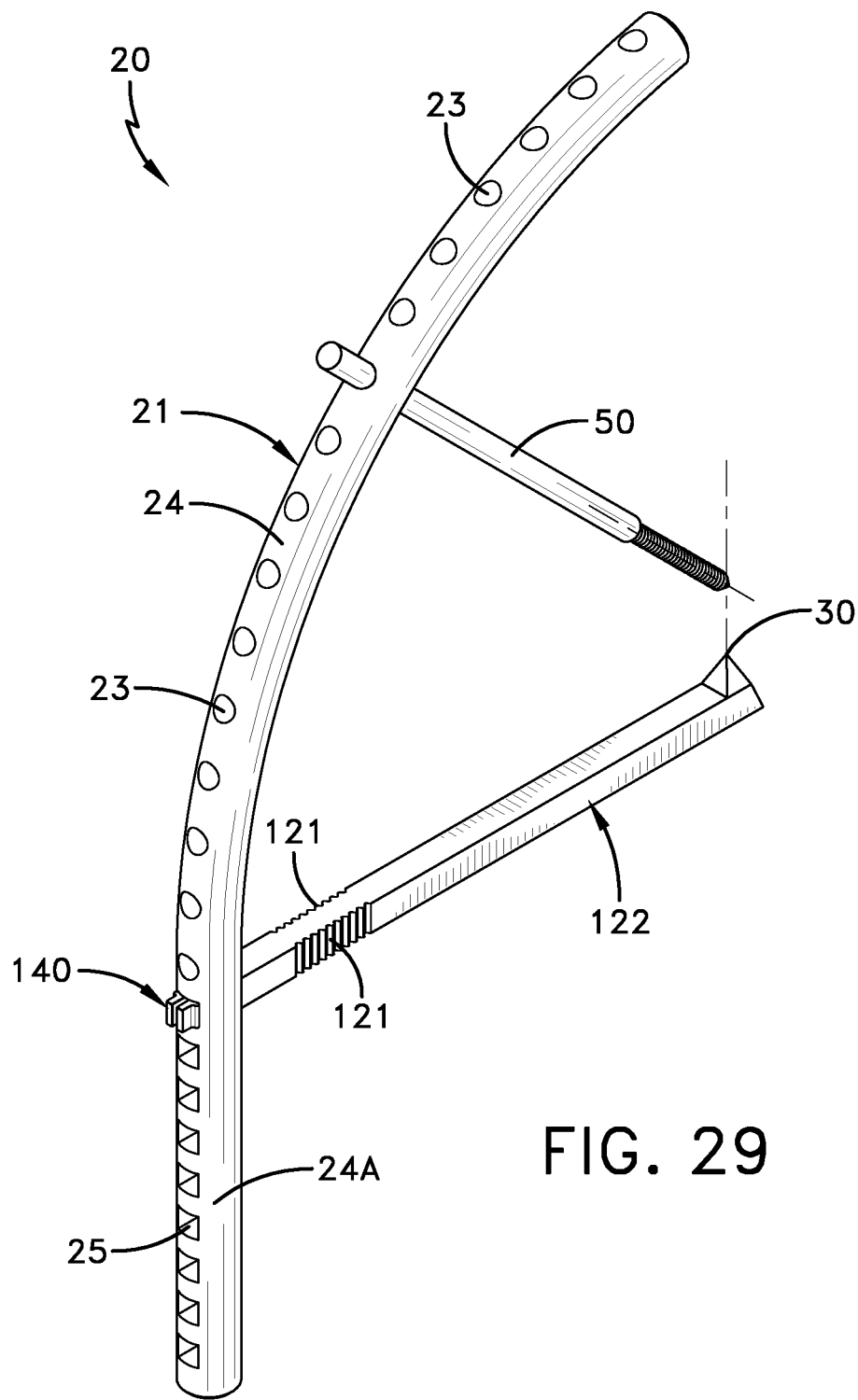
FIG. 29 is a second perspective showing the system from a different perspective.
Figure 30:
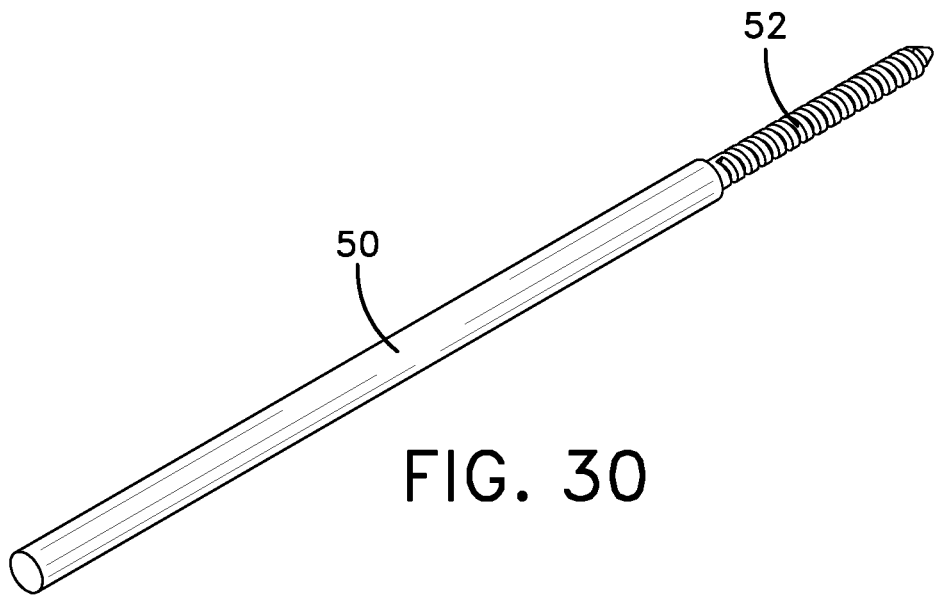
FIG. 30 is an exemplary pin for use with the present invention shown in a perspective view.

In FIGS. 28 and 29, the guide component 21 is shown pass a pin 50 through the opening 23. The opening 23 forms a guide for the pin 50 defining a selected path. The arm 22 is shown attached to the opening or slot 25 of the straight portion 24A. The opening or slots 25 are shown as squares or optionally rectangular openings for holding an attachment end at a second of the arm 22 opposite the virtual localized pinning member 30 at a first end of the arm 22. As shown, the guide component 21 and the arm 22 can be made of metal or any suitable material, more preferably, these parts are injection molded plastic parts designed for one time use after sterilization and disposed of after use. The guide system is greatly simplified in cost while maintaining all the accuracy essential to the described techniques.

Figure 31:
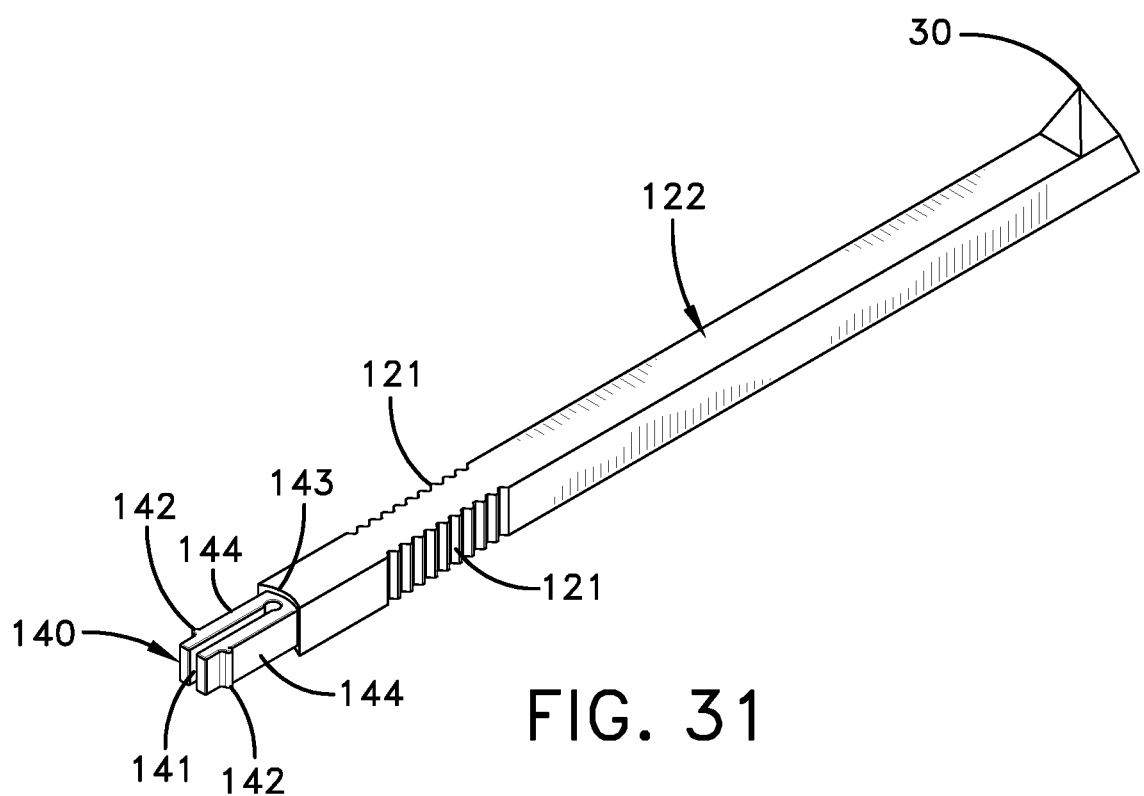
FIG. 31 is an arm with a virtual pin at a first end and an attachment clip at an opposite second end shown in perspective.

The attachment end of the arm is best illustrated in FIG. 31. As shown, a pair of clip arms 140 spaced by a slot 141 are configured to flex when pushed into a square opening or slot 25 and upon full insertion, the arm clears the guide component passing to and abutting a stop 143 and the clip arms 140 return to a clip-on status. Each clip arm 144 has a protrusion 142 to hold the arm tightly in the opening 25 locking it in position. To remove or adjust the arm 22, the clip arms 140 can be squeezed and the arm 22 pulled from the opening 25. To facilitate the insertion or removal of the arm, finger gripping ridges 121 are provided on the body of the arm 22.

In almost all other aspects, the fourth embodiment provides most of the features discussed in the earlier embodiments, with the added advantage of being simple and very inexpensive to manufacture. The arm 22 can be made with a telescoping feature to adjust the location of the virtual pin 30 by moving the telescoping arm 22 in or out a fixed distance.

Figure 32A:
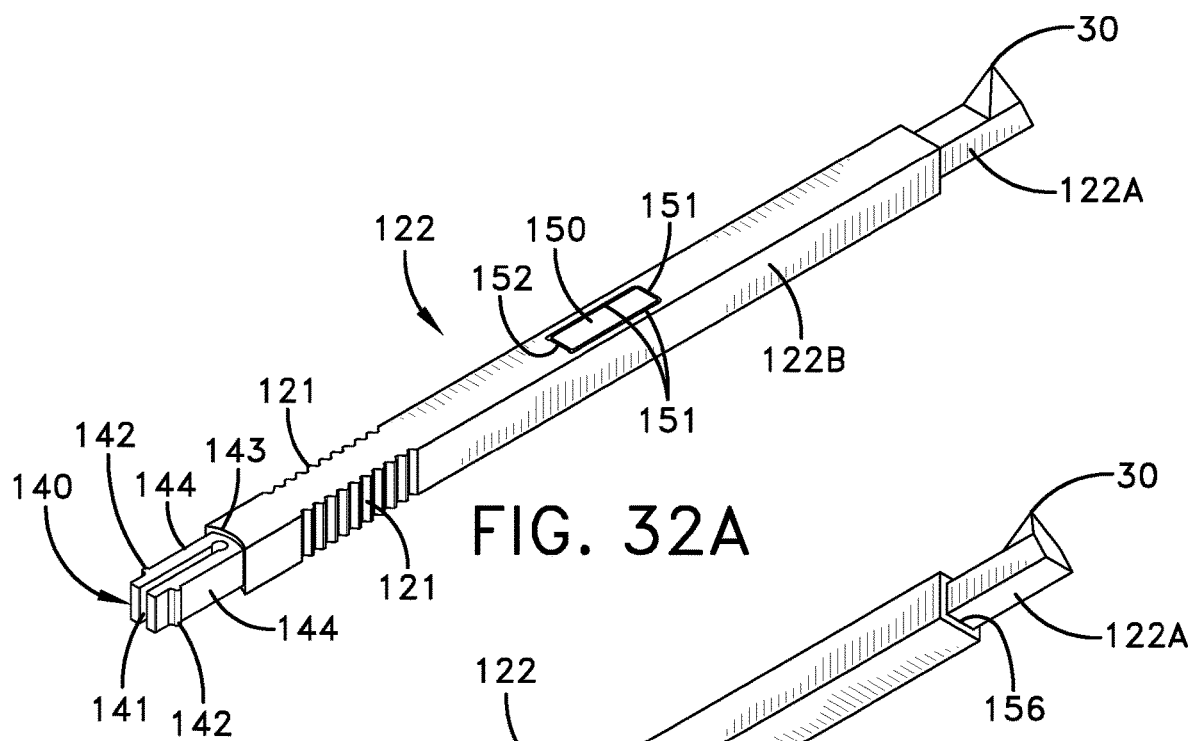
FIGS. 32A-32C shows the arm with a telescoping feature.
Figure 32B:
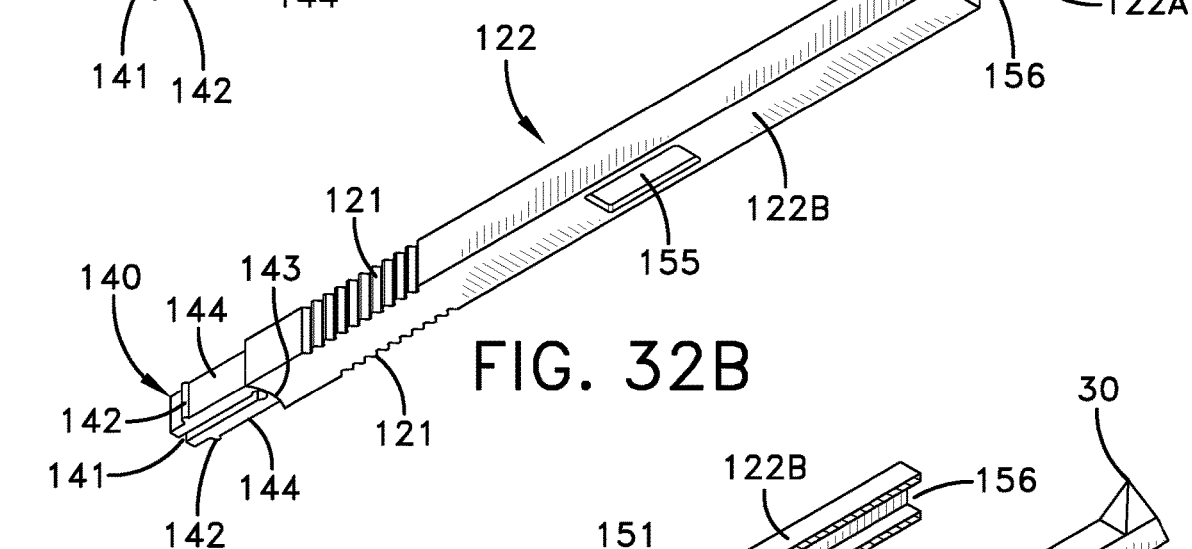
Figure 32C:
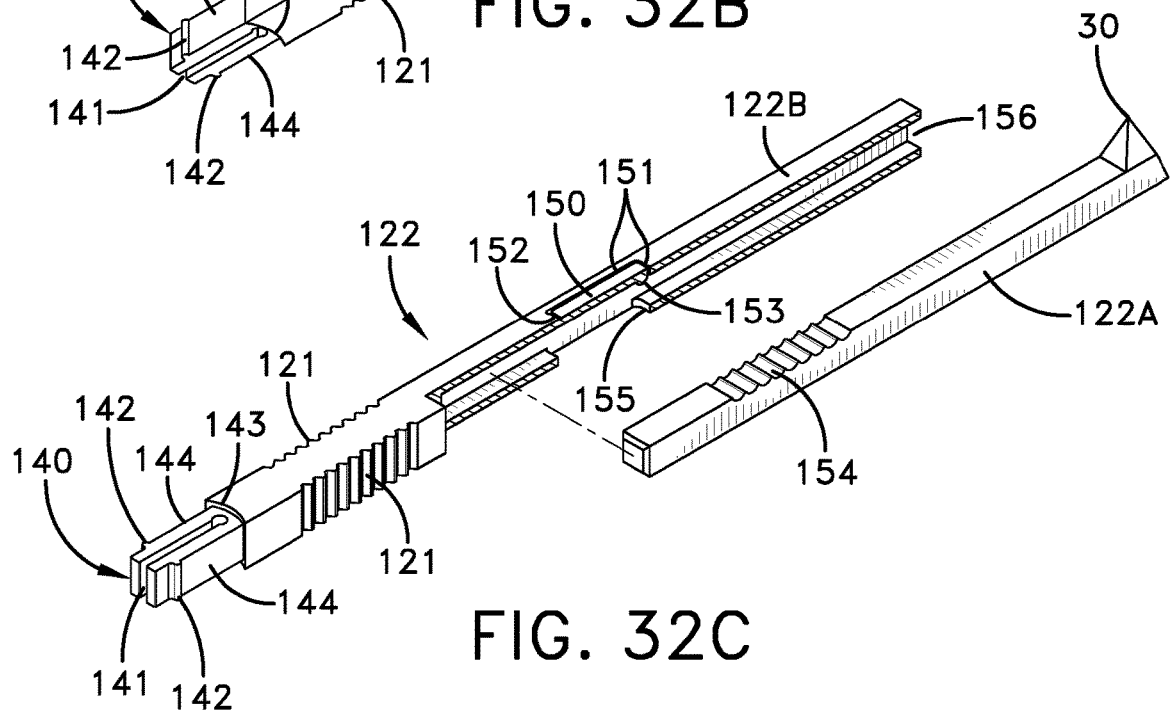

With reference to FIGS. 32A, 32B and 32C, the arm 122 is illustrated as a two-piece assembly having a virtual localizing pin on a first arm portion 122A. The first arm portion 122A as shown is a solid bar that slides inside a tubular hollow second arm portion 122B. The two portions 122A and 122B form a telescoping assembly. The second arm portion 122B has the clip end 140 at an end for attachment to the straight portion of the guide as previously discussed.

As shown in FIG. 32C, the exploded and partial cross-section view of the second arm 122B and the first arm 122A, the first arm portion 122A has a plurality of depressions or notches 154 and the second arm 122B has a living hinged locking feature 150 on one top side and an opening 155. The opening simplifies molding of the living hinged locking feature 150. The locking feature is cut on three sides 151 and hinged at end 152. The opposed end 151 relative to end 152 can have a rounded protrusion 153 configured to fit in the notch 154. In use, the surgeon can move the inner first arm by pulling out or pushing in to adjust the pin 30 location of the arm 122 thereby shifting or offsetting the location of the virtual pathway. It is understood the telescoping feature can be accomplished in a variety of ways and the embodiment shown in FIGS. 32A-32C is simply one of many ways to move the location of the virtual localizing pin 30.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. An instrument guide adapted to carry an instrument used in accessing a compromised portion of a bone structure comprises:
    a first arm having a first referencing arm portion;
    a single piece guide body having a straight portion and a curved or arcuate portion forming a second referencing arm portion;
    the first referencing arm portion having a first end portion, wherein the first end portion of the first referencing arm portion has a reference structure integral therewith and wherein the reference structure defines a virtual access axis; and
    the second referencing arm portion being integral to the first referencing arm portion, the second referencing arm portion having the straight portion and the curved or arcuate portion extending to the straight portion, wherein the virtual access axis is parallel to the straight portion of the second referencing arm portion and extends from the reference structure, the curved or arcuate portion of the second referencing arm portion having at least one guide opening with a guide axis extending to intersect the virtual access axis, the at least one guide opening being at a fixed angle on the second referencing arm portion relative to the virtual axis of the reference structure of the first referencing arm portion.

2. The instrument guide of claim 1 wherein the straight portion of the second referencing arm portion has at least one opening for receiving a second portion of the first referencing arm portion, the at least one opening configured to offset the intersection of the guide axis relative to the virtual access axis by a fixed distance.

3. The instrument guide of claim 2 wherein the offset is set at a fixed distance between 0 to 5 cm on the straight portion of the second referencing arm portion.

4. The instrument guide of claim 2 wherein the offset distance is set at a fixed distance between 1 cm to 5 cm on the straight portion of the second referencing arm portion.

5. The instrument guide of claim 1 wherein the second referencing arm portion has the at least one guide openings located at angular intervals relative to the virtual axis, the fixed angle of one of the at least one guide openings set at 60 degrees on the curved or arcuate portion.

6. The instrument guide of claim 1 wherein the second referencing arm portion has the at least one guide openings located at angular intervals relative to the virtual axis, the fixed angle of one of the at least one guide openings set at 30 degrees on the curved or arcuate portion.

7. The instrument guide of claim 1 wherein the second referencing arm portion has the at least one guide openings located at angular intervals relative to the virtual axis, the fixed angle of one of the at least one guide openings set at 45 degrees on the curved or arcuate portion.

8. The instrument guide of claim 1 wherein the second referencing arm portion has the at least one guide openings located at angular intervals relative to the virtual axis, the fixed angle of a plurality of the at least one guide openings set at 10 degree increments on the curved or arcuate portion.

9. The instrument guide of claim 1 further comprises:
a guide sleeve configured to fit in one of the guide openings, the guide sleeve being coaxially aligned with the guide axis and configured to abut the patient at the location for an entry access, and in combination the referencing structure abutting the patient along the virtual access axis is configured to position and constrain the guide body as an access instrument passing through the guide sleeve forms an entry access passage to the compromised bone structure.

10. The instrument guide of claim 9 wherein the guide sleeve tightly or snugly fits into the guide opening to fix a length between the patient and the guide body.

11. The instrument guide of claim 1 further comprises:
an access instrument with graduations along a shank to establish a depth of an entry access passage into the compromised portion of the bone structure, the access instrument configured to pass through one of the guide openings coaxially aligned with the guide axis.

12. A kit of instrument guides adapted to carry an instrument used in accessing a compromised portion of a bone structure comprising:
a plurality of guide bodies of claim 1, each guide body made as a single piece structure having a distinct angle for the guide opening and a distinct offset at a fixed distance, the kit providing guide openings between 0 and 90 degrees and offsets between 0 and 5 cm.

13. The kit of claim 12 wherein the kit of instrument guides has each guide body having a distinct angle of one of 30, 40, 45, 50 and 60 degrees.

14. The kit of claim 12 wherein the kit of instrument guides has each guide body having a fixed offset of one of 0, 1, 2, 3, 4 or 5 cm.

15. The kit of claim 12 wherein each guide body has a plurality of guide openings set at distinct angles between 0 and 90 degrees and each guide body has a distinct fixed offset relative to the other guide bodies of the kit.

16. The kit of claim 12 further comprises:
a guide sleeve configured to fit in one of the guide openings, the guide sleeve configured to abut the patient at the location for an entry access, and in combination the referencing structure abutting the patient along the virtual axis is configured to position and constrain the guide body as an access instrument passing through the guide sleeve forming the entry access to the compromised bone structure.

17. The kit of claim 12 wherein the guide further comprises:
an access instrument with graduations along a shank to establish a depth of an entry access passage into the compromised portion of the bone structure, the access instrument configured to pass through one of the guide openings coaxially aligned with the guide axis.

18. A method of treating a compromised portion of a bone structure, comprising:
determining a reference location on an exterior surface of the bone structure defining a virtual axis extending through a target location selected by a surgeon, the target location being adjacent to or within the compromised portion of the bone structure;
determining an offset distance selected by the surgeon, the offset distance being along the virtual axis from the reference location to the target location;
determining an access axis extending through the bone structure at a location remote from the reference location and intersecting the target location, wherein the access axis extends through the virtual axis at a position defined by the offset distance; and
forming, at least partially to the target location, an access passage along the access axis from the exterior surface of the bone structure using an access instrument held in a guide opening in a single piece guide body, wherein said forming of the access passage includes mechanically constraining the access instrument relative to the reference location during said forming of the access passage.

19. The method of claim 18, wherein determining the offset distance includes imaging using X-rays, computed tomography (CT) or magnetic resonance imaging (MRI) scans, prior to said forming of the access passage, a mass of the bone structure to identify information characterizing a distance between the target location relative and the reference location using an intersection of lines $L_1$ and $L_2$ creating the desired target location or point $L_{PT}$, $L_1$ being a line projected along the virtual pathway or axis pointing into the compromised portion of the bone structure and $L_2$ being a line along the access axis.

20. The method of claim 18, wherein:
said mechanically constraining the access instrument relative to the reference location includes engaging the access instrument with an instrument guide that is adapted to maintaining the access instrument at a fixed distance relative to the reference location and in a fixed angular orientation relative to the virtual axis;
forming the access passage includes arthroscopically viewing the exterior surface of the bone structure during said forming of the access passage and using said arthroscopic viewing of the exterior surface of the bone structure to maintain a reference structure of the instrument guide in contact with the exterior surface of the bone structure at the reference location thereof.

21. The method of claim 18, wherein said determining of the access axis includes determining an angular orientation of the access axis relative to the virtual axis.

22. The method of claim 18, wherein:
said forming the access axis is performed using an instrument guide; and
said mechanically constraining the access instrument relative to the reference location includes:
engaging the access instrument with the instrument guide;
engaging a reference structure of the instrument guide with
the reference location on the exterior surface of the bone structure; and using the instrument guide to manually manipulate an orientation of the instrument guide such that the virtual axis and the access axis both extend through the target location.

23. The method of claim 22, wherein said mechanically constraining the access instrument relative to the reference location further includes:
engaging the access instrument with a guide opening of the instrument guide while jointly selecting a guide angle and an offset distance adjustor of the instrument guide such that a distance between the reference structure of the instrument guide and a point at which the access axis as defined by the selected guide opening is coaxial with an axis of the guide opening and intersects the virtual axis as defined by the reference structure of the instrument guide is the same as the fixed offset distance.

24. The method of claim 23, wherein the access axis extends through the virtual axis at a position defined by the offset distance.

25. The method of claim 23, wherein
the instrument guide that is adapted to maintaining the access instrument at a fixed distance relative to the reference location and in a fixed angular orientation relative to the virtual axis;
forming the access passage includes arthroscopically viewing the exterior surface of the bone structure during said forming of the access passage and using said arthroscopic viewing of the exterior surface of the bone structure to maintain the reference structure of the instrument guide in contact with the exterior surface of the bone structure at the reference location thereof.

26. The method of claim 25, wherein:
the bone structure includes subchondral bone and cartilage supported thereby; the reference location on the exterior surface of the bone structure is at an exposed surface of the cartilage within an appendage articulation joint; said engaging the reference structure of the instrument guide with the reference location on the exterior surface of the bone structure consists of engaging the reference structure with the exposed surface of the cartilage;
said forming the access passage includes arthroscopically viewing the exposed surface of the cartilage supported by the subchondral bone during said forming of the access passage; and
said mechanically constraining the access instrument relative to the reference location includes using said arthroscopic viewing of the exposed surface of the cartilage to maintain engagement of the reference structure of the instrument guide at the reference location.

27. The method of claim 18, wherein:
said forming the access axis is performed using an instrument guide; said mechanically constraining the access instrument relative to the reference location includes:
engaging the access instrument with a guide opening of the instrument guide; and
jointly selecting the angular orientation of the guide opening and a fixed offset distance of the instrument guide such that a distance between the reference structure of the instrument guide and a point at which the access axis as defined by the angular orientation of the guide opening intersects the virtual axis as defined by the reference structure of the instrument guide is the same as the fixed offset distance; and
said forming the access passage includes manipulating an orientation of the instrument guide such that the virtual axis and the access axis both extend through the target location while maintaining a reference structure of the instrument guide with the reference location on the exterior surface of the bone structure.

28. The method of claim 27, wherein:
the access axis extends coincidental with a longitudinal axis of the guide opening; and
said mechanically constraining the access instrument relative to the reference location includes engaging a portion of the access instrument within the guide opening.

29. The method of claim 27, wherein
the instrument guide that is adapted to maintaining the access instrument at a fixed distance relative to the reference location and in a fixed angular orientation relative to the virtual axis;
forming the access passage includes arthroscopically viewing the exterior surface of the bone structure during said forming of the access passage and using said arthroscopic viewing of the exterior surface of the bone structure to maintain the reference structure of the instrument guide in contact with the exterior surface of the bone structure at the reference location thereof.

30. The method of claim 29, wherein:
the bone structure includes subchondral bone and cartilage supported thereby; the reference location on the exterior surface of the bone structure is at an exposed surface of the cartilage within an appendage articulation joint;
said engaging the reference structure of the instrument guide with the reference location on the exterior surface of the bone structure consists of engaging the reference structure with the exposed surface of the cartilage;
said arthroscopically viewing the exterior surface of the bone structure includes arthroscopically viewing the exposed surface of the cartilage supported by the subchondral bone; and
said mechanically constraining the access instrument relative to the reference location includes using said arthroscopic viewing of the exposed surface of the cartilage to maintain engagement of the reference structure of the instrument guide at the reference location.

* * * * *